(12) United States Patent
Xu

(10) Patent No.: US 11,407,811 B2
(45) Date of Patent: Aug. 9, 2022

(54) FUSION PROTEIN, PREPARATION METHOD THEREFOR AND USE THEREOF

(71) Applicant: JIANGSU RONGTAI BIOTECH CO., LTD., Nanjing (CN)

(72) Inventor: Hanmei Xu, Nanjing (CN)

(73) Assignee: JIANGSU RONGTAI BIOTECH CO., LTD., Nanjing (CN)

( * ) Notice: Subject to any disclaimer, the term of this patent is extended or adjusted under 35 U.S.C. 154(b) by 154 days.

(21) Appl. No.: 16/496,386

(22) PCT Filed: Mar. 5, 2018

(86) PCT No.: PCT/CN2018/077964
§ 371 (c)(1),
(2) Date: Sep. 20, 2019

(87) PCT Pub. No.: WO2018/171410
PCT Pub. Date: Sep. 27, 2018

(65) Prior Publication Data
US 2021/0107968 A1    Apr. 15, 2021

(30) Foreign Application Priority Data
Mar. 20, 2017  (CN) .......................... 201710165059.X

(51) Int. Cl.
| | | |
|---|---|---|
| *C07K 14/705* | (2006.01) | |
| *A61P 27/02* | (2006.01) | |
| *A61P 9/00* | (2006.01) | |
| *A61P 19/02* | (2006.01) | |
| *A61P 27/16* | (2006.01) | |
| *A61P 29/00* | (2006.01) | |
| *A61K 38/00* | (2006.01) | |
| *C07K 14/47* | (2006.01) | |

(52) U.S. Cl.
CPC ........ *C07K 14/70557* (2013.01); *A61K 38/00* (2013.01); *A61P 9/00* (2018.01); *A61P 19/02* (2018.01); *A61P 27/02* (2018.01); *A61P 27/16* (2018.01); *A61P 29/00* (2018.01); *C07K 14/4703* (2013.01); *C07K 2319/30* (2013.01)

(58) Field of Classification Search
CPC ..................... C07K 14/70557; C07K 2319/30
See application file for complete search history.

(56) References Cited

U.S. PATENT DOCUMENTS 7,538,088 B2 * 5/2009 Anderson ............ C07K 14/705
514/1.1

FOREIGN PATENT DOCUMENTS

| WO | WO 0067771 A | 11/2000 |
| WO | WO 2009003145 A | 12/2008 |

OTHER PUBLICATIONS

Mar. 31, 2012 (Mar. 31, 2012), 19(3), pp. 189-194. PU, Chunyan et al. Cloning, Expression, Purification, and, Activity of RGD Modified Peptide EDSM-Y. Pharmaceutical Biotechnology.

* cited by examiner

*Primary Examiner* — Gyan Chandra
(74) *Attorney, Agent, or Firm* — Zhihua Han; Wen IP LLC

(57) ABSTRACT

The invention discloses a fusion protein, preparation method thereof and use thereof and belongs to the field of biopharmaceutical technology. The fusion protein according to the present invention has anti-tumor, anti-autoimmune diseases and anti-inflammatory functions, and therapeutic effects on ophthalmic diseases. According to the long-acting, multi-functional fusion protein of the present invention, the EDSM-Y or EDSM-X polypeptide is fused to the antibody immunoglobulin Fc fragment by a flexible linker so as to obtain the fusion proteins I-V, which can improve the efficacy, prolong the half-life and enhance stability, have characteristics of strong effect, low toxicity and the like, and can be used for the prevention and treatment of solid tumors and various types of inflammation and neovascular ophthalmic diseases. The fusion protein is expressed in a prokaryotic cell or a eukaryotic cell by a genetic engineering method, and the expressed fusion protein is obtained by affinity chromatography.

8 Claims, 4 Drawing Sheets
Specification includes a Sequence Listing.

FUSION PROTEIN, PREPARATION METHOD THEREFOR AND USE THEREOF

CROSS REFERENCE TO RELATED APPLICATION

This application is a national stage application of International application number PCT/CN2018/077964, filed Mar. 5, 2018, titled "FUSION PROTEIN, PREPARATION METHOD THEREOF AND USE THEREOF," which claims the priority benefit of Chinese Patent Application No. 201710165059.X, filed on Mar. 20, 2017, which is hereby incorporated by reference in its entirety.

BACKGROUND

Technical Field

The invention belongs to the field of biopharmaceutical technology, in particular to a fusion protein, a method for preparing the same and application thereof, and more particularly to a series of fusion proteins having anti-tumor, anti-autoimmune diseases, and anti-inflammatory functions and therapeutic effects on ophthalmic diseases.

Related Art

Diseases such as tumors, arthritis, inflammation caused by bacteria, and ophthalmic diseases (such as AMD) are called vascular-related diseases.

In recent years, the incidence and mortality of tumor in China have been increasing. Unrestricted growth, invasion, and metastasis are the signs and characteristics of malignant tumors, and are the main reasons of treatment failure and death. Therefore, controlling growth, invasion and metastasis of tumor is the main measure to improve the prognosis and survival. In 1971, Folkman first proposed the theory that tumor growth depends on angiogenesis. Tumor angiogenesis is the morphological basis of tumor growth and metastasis. It not only provides nutrition to tumors, but also input a large number of tumor cells to the host to cause tumor growth and metastasis. Most malignant solid tumors such as ovarian cancer, liver cancer, cervical cancer and breast cancer are vascular-dependent tumors. On the one hand, new blood vessels provide nutrition and oxygen for tumor growth, and on the other hand, they are important pathways for tumor metastasis. Therefore, inhibition of tumor angiogenesis is an important anticancer measure.

Arthritis-like inflammatory diseases refer to inflammatory diseases that occur in joints and surrounding tissues in human, and can be divided into dozens of types. There are more than 100 million arthritis patients in China, and the number of the patients is increasing. The clinical manifestations are redness, swelling, heat, pain, dysfunction and joint deformity, and in severe cases, joint disability is caused, affecting the quality of life of patients. These mainly include rheumatic arthritis, rheumatoid arthritis, osteoarthritis, gouty arthritis, ankylosing spondylitis, reactive arthritis, infectious arthritis, and the like. Among them, rheumatoid arthritis (RA) is one of the most common inflammatory joint diseases and major cause of disability in clinical. The incidence of RA is about 0.5% to 1.0% in the world, and about 0.4% in China. RA is a chronic systemic inflammatory disease whose cause is not yet clear, with chronic, symmetrical, multiple synovial arthritis and extra-articular lesions as the main clinical manifestations, and is an autoimmune inflammatory disease. Patients often have pain and swelling in the hands or wrists (especially swelling of the back of the wrist) as the initial symptoms, and the symptoms are persistent and cannot be relieved. Although ordinary symptomatic treatment can alleviate the symptoms, the symptoms often relapse due to irregular or insufficient medication. When the disease progresses, obvious morning stiffness may occur, usually up to 1 hour or above, and it always gets worse constantly; at the same time, certain joint dysfunction occurs. Its basic pathological features are vasculitis and synovitis. Intra-articular synovial angiogenesis results in pannus, leading to thickening of the synovial membrane, increase of exudation, secretion of various cytokines, invasion of cartilage, and bone damage. It can also erode the muscle cavity, ligament, tendon sheath and muscles around it, which affects the stability of the joint, and is prone to joint malformation and dysfunction. Vasculitis can also invade all organs of the body, leading to systemic diseases. In the pathological process of arthritis, angiogenesis is a characteristic histological change. Neovascularization is accompanied by synovial hyperplasia and inflammatory cell infiltration, which is the basis of pannus formation and joint destruction. Articular cartilage, which should have no blood vessels, has formed new blood vessels due to some abnormal changes to erode cartilage, causing joint deformation or pain. New blood vessels cause abnormal changes to synovial tissues in patients with rheumatoid arthritis. Therefore, inhibition of neovascularization can alleviate or cure arthritis-like inflammation diseases to a certain extent.

The pathogenesis of iris neovascular eye disease, choroidal neovascular eye disease, retinal neovascular eye disease and corneal neovascular eye disease in ophthalmologic diseases is related to the excessive neovascularization, the inhibition of neovascularization is an important way to treat these diseases, while the proliferation and migration of endothelial cells is an important way to neovascularization. Angiogenesis inhibitors are a class of drugs that have attracted attention in the treatment of neovascular diseases in recent years, and thus blocking the neovascularization may become a new means of treating eye diseases in patients caused by angiogenesis in the eye. Among these angiogenesis inhibitors, especially angiostatin and endostatin attract most attention. Although these angiogenesis inhibitors have very attractive prospects, their defects are also very obvious. That is, the targets of the antiangiogenesis drugs such as endostatin and angiostatin are unclear, their specificity and selectivity for blood vessels are not good enough, and the effect is limited, resulting in a larger amount of drugs used in the experiment. Therefore, a good anti-angiogenic drug should be selective for marker molecules of new blood vessels to achieve a guiding role for the new blood vessels and to enhance the inhibitory effect of drugs on angiogenesis as a whole, so as to realize the effect of high-efficiency angiogenesis inhibition by using only a low dose of drugs. Avastin has been successfully used in the treatment of eye diseases currently, but there is still no such drug independently developed in China. The inhibition of angiogenesis by integrin target of the present invention will be a new option for the treatment of such eye diseases.

In addition, tumors, arthritis-like inflammation, and eye diseases are vascular-related diseases. The growth and metastasis of tumor depend on new blood vessels; inflammation and angiogenesis are two pathological processes that are interrelated and co-developed; ophthalmic diseases such as age-related macular degeneration (AMD) are mainly characterized by choroidal neovascularization.

Neovascularization is highly regulated under normal physiological conditions and is an essential process in reproduction, embryonic development, tissue repair, and wound healing. Angiogenesis also occurs under various pathological conditions, including: tumor growth and metastasis; inflammatory disorders such as rheumatoid arthritis, psoriasis, osteoarthritis, inflammatory bowel disease, Crohn's disease, ulcerative colitis and other inflammatory disorders.

Integrins are a class of receptors that are widely distributed on the cell surface, which can mediate the adhesion between cells and extracellular matrixes as well as the adhesion between cells. They participate in angiogenesis by linking the interaction between intracellular cytoskeletal proteins and extracellular matrix molecules. Recently, at least eight integrins ($\alpha1\beta1$, $\alpha2\beta1$, $\alpha3\beta1$, $\alpha6\beta1$, $\alpha6\beta4$, $\alpha5\beta1$, $\alpha v\beta3$, $\alpha v\beta5$) are involved in angiogenesis, wherein $\alpha v\beta3$ plays an important role. $\alpha v\beta3$ can recognize the Arg-Gly-Asp (RGD) sequence in a ligand molecule. $\alpha v\beta3$ can be expressed in a variety of cell types and participates in physiological and pathological processes such as tumor angiogenesis, invasion, metastasis, inflammation, wound healing and coagulation in combination with multiple ligands in multicellular activity. Therefore, an RGD sequence-containing polypeptide can function as an integrin antagonist, and the RGD sequence can be used as a carrier which targeted transport to the neovascular endothelium to more efficiently treat neovascular diseases. Therefore, the antiangiogenesis polypeptide can prevent the delivery of oxygen and nutrition to the synovial membrane by inhibiting angiogenesis, and can also directly causes the blood vessel degeneration, thereby possibly inhibiting the synovial proliferation of the RA. The inhibition of neovascularization is an important way to treat these diseases, while the proliferation and migration of endothelial cells is an important way to neovascularization.

Antibody drugs are the focus and hotspot of current drug research and development, usually can get a marketing license faster, and bring greater commercial success. With the successful platform of traditional antibodies, a new functional fusion protein has also developed rapidly, which fuses proteins or polypeptides with immunoglobulin Fc fragments, based on antibody structure. Fc fusion protein refers to a novel protein molecule produced by linking and fusion of a functional protein molecule with biological activity, a polypeptide molecule and an immunoglobulin Fc fragment through a special linker with a technique such as genetic engineering, and the functional protein formed can bind to soluble ligand (or receptor) molecules of endogenous receptors (or ligands) or other active substances (i.e. cytokines) that require an prolonged half-life. Such fusion proteins not only retain the biological activity of functional protein molecules, but also have some antibody properties, such as a long half-life. For example, the half-life of a common recombinant IL-2 in vivo is only 6.9 min, while the circulating half-life of a recombinant IL-2/Fc fusion protein in vivo is nearly 700-fold longer. The Fc fusion protein can be classified into cyto-lytic and non-lytic depending on whether it is desired to exert the biological activity of the Fc segment binding to Fc$\gamma$R to mediate antibody-dependent cell mediated cytotoxicity (ADCC) or binding to complement C1q to mediate complement-dependent cytotoxicity (CDC). The former is formed by fusion of a functional protein and a Fc fragment which is natural or has increased activity, which not only has the biological activity and long plasma half-life of the functional protein, but also retains the ability of the Fc segment to mediate ADCC and CDC effects, and can realize targeted killing of functional protein receptor positive cells. In the field of antibody application, especially antibodies with anti-tumor activity, the amino acid composition or glycosylation pattern of the Fc segment are optimized to enhance ADCC, CDC and the like mediated by them. A non-lytic fusion protein is a fusion of a functional protein and a Fc fragment with reduced activity, and the binding affinity of the Fc to relevant receptors is modulated by mutational modification of the complement receptor binding domain or glycosylation pattern on the Fc fragment to reduce or eliminate the ADCC and CDC effects, and retains only the biological activity of the functional protein and the long half-life of the Fc segment without cytotoxicity. For example, the researchers fused a hybrid Fc (hyFc) consisting of IgD and IgG4 with erythropoietin (EPO) to construct a long-acting EPO-hyFc molecule that cannot bind to Fc$\gamma$R I and C1q, and is not cytotoxic. Its half-life is twice that of recombinant human EPO-darbepoetin alfa. In addition to long-acting properties, Fc fragments also can increase molecular stability. Fusion with Fc can increase the expression of the protein in mammalian cells. On the other hand, the Fc fragment can specifically bind to a Protein A affinity column and simplify the purification step of the Fc fusion protein, which is of great significance in the research and development of related biological products.

SUMMARY

1. Problem to be Solved

In view of the high chemical synthesis cost, short half-life, and single target of the existing polypeptide, one of the objects of the present invention is to provide a fusion protein comprising an integrin $\alpha v\beta3$ ligand sequence, an antiangiogenesis polypeptide sequence, and Fc sequence of an antibody IgG1 or IgG2 or IgG4 or HyFc, and the sequences are linked by a flexible amino acid linker, which can form a correct high-order structure, with the advantages of long half-life and high antitumor activity.

Another object of the present invention is to provide a method for preparing the fusion protein, which links two different active polypeptides by using mammalian cell expression methods, instead of chemical synthesis methods, and is expected to solve the problems that polypeptide molecules having polyamino acid chain, a secondary structure such as a disulfide bond, and a high-order structure being difficult to synthesize, low in production yield and high in synthesis cost; improving the affinity of the polypeptide molecule to the target and the cytotoxicity of the polypeptide molecule, and enhancing the therapeutic effect of the polypeptide molecule; as well as overcoming the shortcomings of short half-life and frequent administration of the polypeptide molecule.

2. Technical Solution

In order to solve the above problems, the technical solution adopted by the present invention is as follows.

A fusion protein comprising an integrin $\alpha v\beta3$ ligand sequence, an antiangiogenesis polypeptide sequence, and an Fc sequence of an antibody IgG1 or IgG2 or IgG4 or HyFc is provided.

There are two antiangiogenesis polypeptide sequences, respectively EDSM-X and EDSM-Y, in the present invention; in the sequence listing, SEQ ID NO: 1 is the integrin $\alpha v\beta3$ ligand sequence, and SEQ ID NO: 3 is an amino acid sequence corresponding to EDSM-Y, SEQ ID NO: 5 is an amino acid sequence corresponding to EDSM-X, SEQ ID NO: 7 is an amino acid sequence corresponding to IgG1-Fc, SEQ ID NO: 9 is an amino acid sequence corresponding to IgG2-Fc, SEQ ID NO: 11 is an amino acid sequence corresponding to mIgG4-Fc, and SEQ ID NO: 13 is an amino acid sequence corresponding to hyFc.

Further, the amino acid sequences corresponding to the series of fusion proteins are SEQ ID NO: 15, SEQ ID NO: 17, SEQ ID NO: 19, SEQ ID NO: 21, and SEQ ID NO: 23, respectively, wherein the antiangiogenesis polypeptide sequence constituting the amino acid sequence SEQ ID NO: 15, SEQ ID NO: 17, and SEQ ID NO: 19 is linked to the antibody sequence by a flexible amino acid linker, and the polypeptides at both ends can be changed and shifted.

SEQ ID NO: 15 is formed by IgG1-Fc linked to an antiangiogenesis polypeptide EDSM-Y via a flexible linker, and the structural schematic diagram is as shown in FIG. 1.

SEQ ID NO: 17 is formed by IgG2-Fc linked to an antiangiogenesis polypeptide EDSM-Y via a flexible linker, and the structural schematic diagram is shown in FIG. 2.

SEQ ID NO: 19 is formed by mIgG4-Fc linked to an antiangiogenesis polypeptide EDSM-Y via a flexible linker, and the structural schematic diagram is shown in FIG. 3.

SEQ ID NO: 21 is formed by hyFc linked to an antiangiogenesis polypeptide EDSM-Y via a flexible linker, and the structural schematic diagram is shown in FIG. 4.

SEQ ID NO: 23 is formed by hyFc directly linked to antiangiogenesis polypeptides EDSM-Y and EDSM-X, and the structural schematic diagram is shown in FIG. 5.

For the genes encoding the above fusion proteins, the nucleic acid sequences encoding SEQ ID NO: 15, SEQ ID NO: 17, SEQ ID NO: 19, SEQ ID NO: 21, and SEQ ID NO: 23 are SEQ ID NO: 16, SEQ ID NO: 18, SEQ ID NO: 20, SEQ ID NO: 22 and SEQ ID NO: 24, respectively.

Use of the above fusion proteins in the preparation of a medicament for treating tumors, autoimmune diseases, inflammations and ophthalmic diseases is provided.

Further, the tumors include gastric cancer, lung cancer, liver cancer, breast cancer, colon cancer, glioma, melanoma, and cervical cancer, as well as primary or secondary cancer, melanoma, and sarcoma originating from the head and neck, brain, thyroid, esophagus, pancreas, lung, liver, stomach, breast, kidney, gallbladder, colon or rectum, ovary, cervix, uterus, prostate, bladder, and testicle in human.

Further, the inflammations include rheumatoid arthritis, osteoarthritis, gouty arthritis, ankylosing spondylitis, psoriatic arthritis, reactive arthritis, infectious arthritis, and traumatic arthritis; the autoimmune diseases include lupus erythematosus and psoriasis.

Further, the ophthalmic diseases include iris neovascular eye disease, choroidal neovascular eye disease, retinal neovascular eye disease, or corneal neovascular eye disease.

Further, the iris neovascular eye disease includes iris neovascular eye diseases caused by neovascular glaucoma, diabetic retinopathy or central retinal vein occlusion; the choroidal neovascular eye disease includes age-related macular degeneration, central exudative chorioretinopathy, ocular histoplasmosis syndrome or serpiginous choroidopathy; the retinal neovascular eye disease includes the retinal neovascular eye diseases associated with diabetes, tumors, retinal detachment, central retinal vein occlusion, retinal periphlebitis, systemic lupus erythematosus, Eales diseases or Coat diseases; the corneal neovascular eye disease includes the corneal neovascular eye diseases caused by cornea contacting an lens, as well as the corneal neovascular eye diseases caused by alkali and other chemical burns, corneal surgery, bacterial infection, chlamydial infection, viral infection or protozoal infection.

Further, the dosage form of the medicament is a capsule, a tablet, a pill, an injection, a nasal spray or an aerosol.

A preparation method of the above fusion proteins includes a synthesis method and a method of recombinant expression by *Escherichia coli*, yeast, and mammalian cells.

3. Beneficial Effect

Compared with the prior art, the beneficial effects of the present invention are as follows.

(1) The present invention obtains a series of fusion proteins by fusion of an EDSM-Y polypeptide and an antibody immunoglobulin Fc fragment via a flexible (F) linker. The problems of synthesis bottleneck of a polypeptide molecule having a large molecular weight and a complex structure, in particular macromolecular polypeptide molecules having a secondary structure such as a disulfide bond and a high-order structure are solved; the technical bottleneck of chemical synthesis difficulty and low yield of a large molecular weight polypeptide is overcome, and the production cost of the macromolecular polypeptide is significantly reduced; the expression of a polypeptide molecule by a living body cell such as a mammalian cell can form a correct high-order structure, and the affinity of the polypeptide molecule to the target molecule is superior to that of the chemically synthesized polypeptide molecule; the polypeptide molecule forms a fusion protein molecule with the Fc fragment of antibody IgG1, IgG2 or IgG4, and the Fc fragment of IgG is prevented from being degraded by a Fc receptor (FcRn)-mediated recycling mechanism, while the Fc fragment has a larger molecular weight and low renal clearance, so as to ensure that the half-life of the fusion protein is significantly longer than that of the polypeptide, and at the same time, the fusion protein formed by the fusion of the Fc fragment of IgG1 can increase the cytotoxicity of ADCC and CDC, and can significantly increase the activity of anti-tumor molecules, and its anti-tumor effect is superior to that of polypeptide molecules; and the eukaryotic expression system is used to link the antibody Fc fragment to the EDSM-Y sequence by linker to prolong the half-life of the functional protein EDSM-Y.

(2) The fusion protein of the present invention is a class of integrin blocker polypeptide drugs, which can effectively inhibit angiogenesis to achieve the functions of anti-tumor, and treatment of arthritis and inflammation-related ophthalmic diseases.

(3) The fusion protein sequence of the present invention includes an arginine-glycine-aspartate (RGD) sequence, the RGD sequence is an important ligand of integrin, and the RGD sequence-containing polypeptide Gly-Gly-Gly-Gly-Arg-Gly-Asp can specifically recognize integrins, can effectively inhibit neovascularization, and can be used to treat tumor diseases, arthritis diseases and ophthalmic diseases. The present invention uses a flexible linker to link the two polypeptides EDSM-Y and the Fc fragment of the antibody to obtain the amino acid sequences of the fusion protein: SEQ ID NO: 15, SEQ ID NO: 17, SEQ ID NO: 19, SEQ ID NO: 21, and SEQ ID NO: 23, which can improve the efficacy, prolong the half-life, enhance stability, and make the fusion protein have certain ADCC and CDC effects at the same time, and have the characteristics of strong effect and low toxicity.

(4) The fusion protein of the present invention can be targeted to the neovascular endothelium, and inhibit neovascularization to achieve the effects of preventing or treating vascular and inflammation-related diseases.

(5) The present invention has an effect of inhibiting various tumors in terms of anti-tumor, and it can be seen from the MTT assay results in Example 2 that the fusion protein I, fusion protein II, fusion protein III, fusion protein IV and fusion protein V can effectively inhibit proliferation of gastric cancer, lung cancer, liver cancer, breast cancer, melanoma, colon cancer, glioma and cervical cancer, the inhibition rate on melanoma, gastric cancer and lung cancer reaches 50% or more at the concentration of 32 μg/mL; the inhibition rate on glioma and cervical cancer reaches 40% or more at the concentration of 64 μg/mL; higher concentration is needed for effective inhibition of colon cancer, liver cancer and breast cancer cells.

(6) According to the present invention, in terms of inhibiting the neovascularization, it can be clearly seen from the cell migration experiment of Example 3 that the inhibition of migration of HUVEC is significant at a concentration of 2 μg/mL, and the inhibition rate reaches 70% or more.

(7) According to the present invention, in terms of autoimmune diseases and anti-inflammatory effects, it can be clearly seen from a series of verification model experiments of Examples 4-10 that fusion protein I, fusion protein II, fusion protein III, fusion protein IV and fusion protein V can significantly inhibit lymphocyte proliferation, inhibit IL-1β inflammatory factors production by macrophages, inhibit granuloma formation, reduce capillary permeability in model groups, inhibit ear swelling and toe swelling in model groups, and reduce the degree of chronic inflammation of adjuvant arthritis in rats.

(8) According to the present invention, in terms of the treatment of ophthalmic diseases, it can be seen from Examples 11-19 that fusion protein I, fusion protein II, fusion protein III, fusion protein IV and fusion protein V can significantly inhibit proliferation of human retinal vascular endothelial cells, inhibit the neovascularization of chicken embryo chorioallantoic membrane, inhibit the growth of corneal new blood vessels, inhibit the growth of iris new blood vessels in rabbits, promote the increase of choroidal blood flow in rabbit eyes, reduce the retinal neovascular plexus in oxygen-induced retinopathy (OIR) mice and inhibit neovascularization in oxygen-induced neonatal rat retinopathy model and has a certain therapeutic effect on diabetic retinopathy.

DETAILED DESCRIPTION

The invention is further described below in conjunction with specific examples.

Example 1

(I) Acquisition of Fusion Protein Gene and Construction of Expression Vector

The fusion protein domain of the present invention comprises an integrin αvβ3 ligand sequence, an antiangiogenesis polypeptide sequence, and an Fc sequence of an antibody IgG1 or IgG2 or IgG4 or HyFc, where the antiangiogenesis polypeptide sequence is EDSM-X and EDSM-Y, respectively; in the sequence listing, SEQ ID NO: 1 is the integrin αvβ3 ligand sequence, SEQ ID NO: 3 is an amino acid sequence corresponding to EDSM-Y, SEQ ID NO: 5 is an amino acid sequence corresponding to EDSM-X, SEQ ID NO:7 is an amino acid sequence corresponding to IgG1-Fc, SEQ ID NO: 9 is an amino acid sequence corresponding to IgG2-Fc, SEQ ID NO: 11 is an amino acid sequence corresponding to mIgG4-Fc, and SEQ ID NO: 13 is an amino acid sequence corresponding to hyFc.

Figure 1:
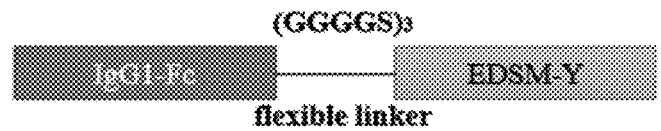
FIG. 1 is a structural schematic diagram of a fusion protein corresponding to SEQ ID NO: 15 according to the present invention, wherein the linker GGGGSGGGGSGGGGS corresponds to SEQ ID NO: 25.
Figure 2:
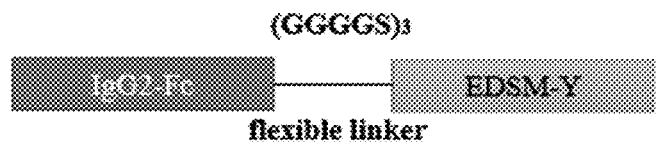
FIG. 2 is a structural schematic diagram of a fusion protein corresponding to SEQ ID NO: 17 according to the present invention, wherein the linker GGGGSGGGGSGGGGS corresponds to SEQ ID NO: 25.
Figure 3:
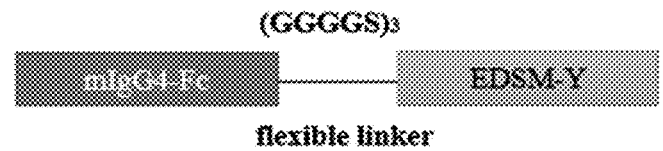
FIG. 3 is a structural schematic diagram of a fusion protein corresponding to SEQ ID NO: 19 according to the present invention, wherein the linker GGGGSGGGGSGGGGS corresponds to SEQ ID NO: 25.
Figure 4:
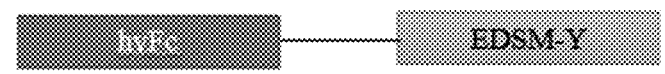
FIG. 4 is a structural schematic diagram of a fusion protein corresponding to SEQ ID NO: 21 according to the present invention.
Figure 5:
FIG. 5 is a structural schematic diagram of a fusion protein corresponding to SEQ ID NO: 23 according to the present invention.

The human immunoglobulin Fc region and its mutant are ligated to the EDSM-Y protein by GGGGS×3 Linker to design five novel Fc fusion proteins Fc-EDSM-Y, which are named as protein I, protein II, protein III, protein IV, and protein V respectively in the following experiments; amino acid sequences corresponding to protein I, protein II, protein III, protein IV, and protein V are SEQ ID NO: 15, SEQ ID NO: 17, SEQ ID NO: 19, SEQ ID NO: 21, and SEQ ID NO: 23, respectively, where SEQ ID NO: 15 is formed by IgG1-Fc linked to an antiangiogenesis polypeptide EDSM-Y via a flexible linker, and the structural schematic diagram is as shown in FIG. 1; SEQ ID NO: 17 is formed by IgG2-Fc linked to an antiangiogenesis polypeptide EDSM-Y via a flexible linker, and the structural schematic diagram is shown in FIG. 2; SEQ ID NO: 19 is formed by mIgG4-Fc linked to an antiangiogenesis polypeptide EDSM-Y via a flexible linker, and the structural schematic diagram is shown in FIG. 3; SEQ ID NO: 21 is formed by hyFc directly linked to an antiangiogenesis polypeptide EDSM-Y, and the structural schematic diagram is shown in FIG. 4; SEQ ID NO: 23 is formed by hyFc directly linked to antiangiogenesis polypeptides EDSM-Y and EDSM-X, and the structural schematic diagram is shown in FIG. 5. According to the codon preference of CHO cells, the coding sequences of five novel Fc fusion proteins Fc-EDSM-Y are optimized, and the EcoRI enzyme cleavage sites, Kozak sequences, signal peptides are introduced at the 3' end, and XhoI enzyme cleavage sites are introduced at the 5' end. The DNA sequence is obtained by a whole gene synthesis method, and the nucleic acid sequences encoding SEQ ID NO: 15, SEQ ID NO: 17, SEQ ID NO: 19, SEQ ID NO: 21, and SEQ ID NO: 23 are sequentially SEQ ID NO: 16, SEQ ID NO: 18, SEQ ID NO: 20, SEQ ID NO: 22, and SEQ ID NO: 24, respectively.

The DNA sequences of the above five fusion proteins Fc-EDSM-Y were synthesized by a commissioned biotechnology company, ligated to a pUC57 vector to form a cloning vector, and stored in E. coli DH5a to form a clone strain, which was sent as bacteria penetrans. The five fusion proteins all used pcDNA3.4/MCS(+) as the expression vectors, and the vector construction processes were completely identical. Therefore, IgG1-Fc/EDSM-Y was taken as an example, and the experimental procedures were as follows.

1. Under sterile conditions, the IgG1-Fc/EDSM-Y clone strain sent by the biotechnology company was picked up from the surface of the bacteria penetrans and inoculated into two tubes containing 5 mL of Amp-resistant LB medium at 37° C., 120 rpm under shaking overnight.

2. After the culture of the bacteria solution in the two tubes, 2.5 mL of sterile 60% glycerol was added in one tube, mixed well, and then charged into sterile centrifuge tubes, with 1 mL per tube, to prepare glycerin tubes, which were frozen and stored at −80° C. The bacteria solution in the other tube was centrifuged at 12,000 rpm for 1 min to collect thalli, and a cloning vector of IgG1-Fc/EDSM-Y was extracted by using a conventional commercial plasmid miniprep kit.

Figure 6:
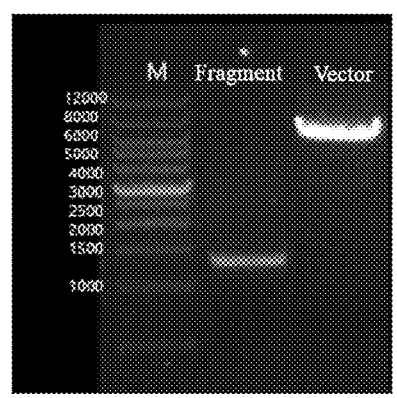
FIG. 6 is an electrophoretogram of a fragment obtained by recovering IgG1-Fc/EDSM-Y and expression vector pcDNA3.4/MCS(+) gel according to the present invention.

3. The restriction endonuclease EcoRI/XhoI was used to perform double enzyme digestion of the IgG1-Fc/EDSM-Y cloning vector and the expression vector pcDNA3.4/MCS(+), and the inserted fragment IgG1-Fc/EDSM-Y having cohesive ends and the expression vector pcDNA3.4/MCS(+) were separated by horizontal nucleic acid electrophoresis and recovered using a commercial DNA gel recovery kit. The DNA fragment recovery results are shown in FIG. 6.

4. Using the T4 ligase, the inserted fragment IgG1-Fc/EDSM-Y and the expression vector pcDNA3.4/MCS(+) obtained by gel recovery were ligated at 16° C. according to the molar ratio of inserted fragment to vector of 1:5 for 16 h.

5. 20 uL DNA ligation was added to 100 uL of freshly thawed E. coli TOP10 competent cells, mixed gently, and placed in an ice bath for 30 min. After being heat-shocked at 42° C. for 45 s, the mixture was quickly placed in an ice bath for 2 to 3 minutes. 900 uL of non-resistant LB medium was added to the mixture, and cultured at 37° C. for 1 h with shaking. The mixture was centrifuged at 4500 rpm for 1 min at 4° C., 900 uL of supernatant was discarded under sterile conditions, the remaining bacterial solution and the precipitated thalli were mixed evenly via gentle blowing-suction, all of which was aspirated by a pipette, and coated to an Amp-resistant LB solid plate and statically cultured at 37° C. for 12 h.

6. 20 single colonies were picked up and inoculated in a tube containing 5 mL of Amp-resistant LB medium, and cultured at 37° C., 120 rpm under shaking overnight.

Figure 7:
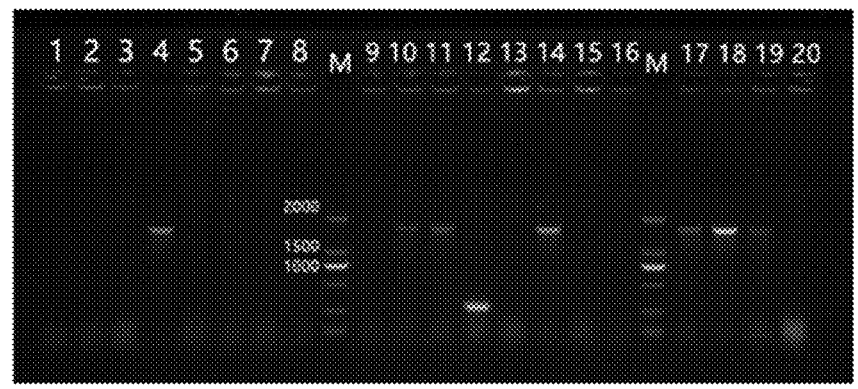
FIG. 7 is a diagram showing the results of PCR verification of bacterial liquid according to the present invention.

7. Among the strains inoculated in the previous step, each of normally growing strains was stored in 3 glycerol tubes. At the same time, each strain was tested by bacterial PCR verification (see FIG. 7), positive clones were screened, and the preserved glycerol tubes were sent to the biotechnology company for sequencing verification. The correct expression vector was finally obtained.

8. The glycerol tubes preserving the strain having correct sequencing was taken out, inoculated into a 250 mL shake flask containing 30 mL of Amp-resistant LB medium, cultured at 37° C., 120 rpm overnight, stored in 20 glycerol tubes which were stored at −80° C. At this point, the construction of the IgG1-Fc/EDSM-Y expression vector was finished.

(II) Expression of Fusion Protein

Transient transfection is one of the ways to introduce DNA into eukaryotic cells. In transient transfection, recombinant DNA is introduced into highly infectious cell lines to obtain transient but high levels of expression of the target gene. Enough proteins can be obtained for experiments in a short period of time, saving cell screening time in stable transfection. The Expi293 Expression System is used to express five novel fusion proteins Fc-EDSM-Y. Since the expression process of the fusion protein is completely identical, the IgG1-Fc/EDSM-Y is used as an example. The experimental procedures are as follows.

1. Plasmid preparation.

A glycerol tube preserving strain with IgG1-Fc/EDSM-Y expression vector was taken from a −80° C. refrigerator, inoculated into a 2 L shake flask containing 500 mL of Amp-resistant LB medium, and cultured at 37° C., 160 rpm under shaking overnight.

After the completion of the culture, the mixture was centrifuged at 5000 g for 5 min to collect thalli, and the plasmid was extracted using a commercial EndoFree Plasmid Maxi Kit. The plasmid concentration was controlled to be 1 mg/mL or above (if it is lower than this concentration, concentration is required), and then sterilized by filtration using a sterile 0.22 µm pore size filter to complete plasmid preparation.

2. Early-Stage Preparation of Transient Transfection of Cells

The 293F cells used for transfection were passaged at a cell density of $0.4*10^6$ cells/mL for every four days from the day of thawing, and at least three passages were performed, followed by the transient transfection. During the passage, the passage volume was expanded as needed based on the volume of the final transfection medium.

3. Transient Transfection (Taking 30 mL Transfection Volume as an Example, Multiply as Needed)

(1) One day before the experiment, $6*10^7$ live cells were inoculated into 30 mL of Expi293 Expression Medium, and cultured at 37° C., 8% $CO_2$, 125 rpm under shaking.

(2) On the day of the experiment, the cells cultured on the previous day were counted firstly, the cell density should be $3-5*10^6$ cells/mL, and the viability was greater than 95%.

(3) $7.5*10^7$ cells were aspirated into a new 125 mL Erlenmeyer flask and the preheated Expi293 Expression Medium was added to 25.5 mL.

(4) Preparation of Plasmid-Transfection Reagent Mixture a. 30 µg of plasmid DNA was re-dissolved in 1.5 mL of Opti-MEM I Reduced Serum Medium and mixed gently.

b. 81 µL of ExpiFectamine 293 Reagent was added to Opti-MEM I Reduced Serum Medium to a volume of 1.5 mL. The mixture was gently mixed and incubated for 5 min at room temperature (long incubation period affects conversion efficiency).

c. The above two solutions were mixed gently, incubated for 20-30 min at room temperature to complete the preparation of the plasmid-transfection reagent mixture.

(5) 3 mL of plasmid-transfection reagent mixture was added to the cell culture liquid of step (3) to 28.5 mL in total.

(6) The mixture was cultured at 37° C., 8% $CO_2$, 125 rpm under shaking for 20 h.

(7) 150 µL of ExpiFectamine 293 Transfection Enhancer 1 and 1.5 mL of ExpiFectamine 293 Transfection Enhancer 2 were added. At this point, the total volume was 30 mL.

(8) The mixture was cultured at 37° C., 8% $CO_2$, 125 rpm under shaking. The culture was terminated after 6 days and protein purification was carried out.

(III) Purification of Fusion Protein

Protein A is a cell-wall protein isolated from *Staphylococcus aureus*, which binds to mammalian IgG mainly through the Fc fragment and has very high specificity and binding ability, and is widely used for purification of IgG antibodies and IgG-Fc fusion proteins. The five novel fusion proteins Fc-EDSM-Y have IgG-Fc fragments and thus the purification processes are completely identical. Therefore, IgG1-Fc/EDSM-Y produced by transient transfection at 1.6 L scale is used as an example. The experimental procedures are as follows.

1. Sample pretreatment: 1.6 L of transiently transfected cell culture liquid after culture termination was centrifuged at 7500 rpm for 20 min at 4° C., and the supernatant obtained was about 1.46 L for the next protein A capture.

Figure 8:
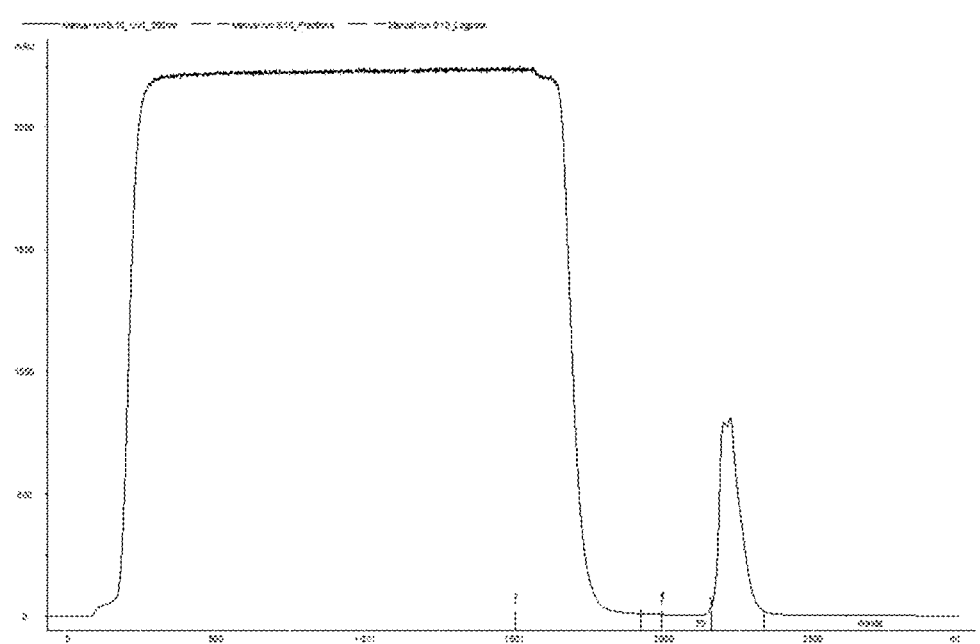
FIG. 8 is a diagram showing the results of capture of fusion protein according to the present invention.

2. Affinity capture of target protein (See FIG. 8)

The column information is as follows:

| Packing | Mabselect SuRe |
| --- | --- |
| Column | XK50/20 |
| Column height (cm) | 10 |
| Cross-sectional area of column (cm²) | 19.62 |
| Packing volume (mL) | 196.2 |

(1) The sterilization was first performed with 500 mL of 0.2 M NaOH at a flow rate of 10 mL/min.

(2) The column was equilibrated with 20 mM PB and 0.15 M NaCl, pH 7.0, the volume was about 1000 mL, and the flow rate was 20 mL/min.

(3) Loading: the sample was pre-adjusted to a neutral pH, and the flow rate was 20 mL/min.

(4) The column was washed with 20 mM PB and 0.15 M NaCl, pH 7.0, the volume was about 800 mL, and the flow rate was 20 mL/min.

(5) The target protein was eluted with 50 mM citric acid-sodium citrate, and 0.15 M NaCL, pH 3.0, collection was started at onset 20 mAu and stopped at post-peak 20 mAu; and the flow rate is 20 mL/min.

(6) The column was finally washed with 500 mL of 0.2 M NaOH, and rinsed with water to neutral, and the column was stored with 20% ethanol.

Figure 9:
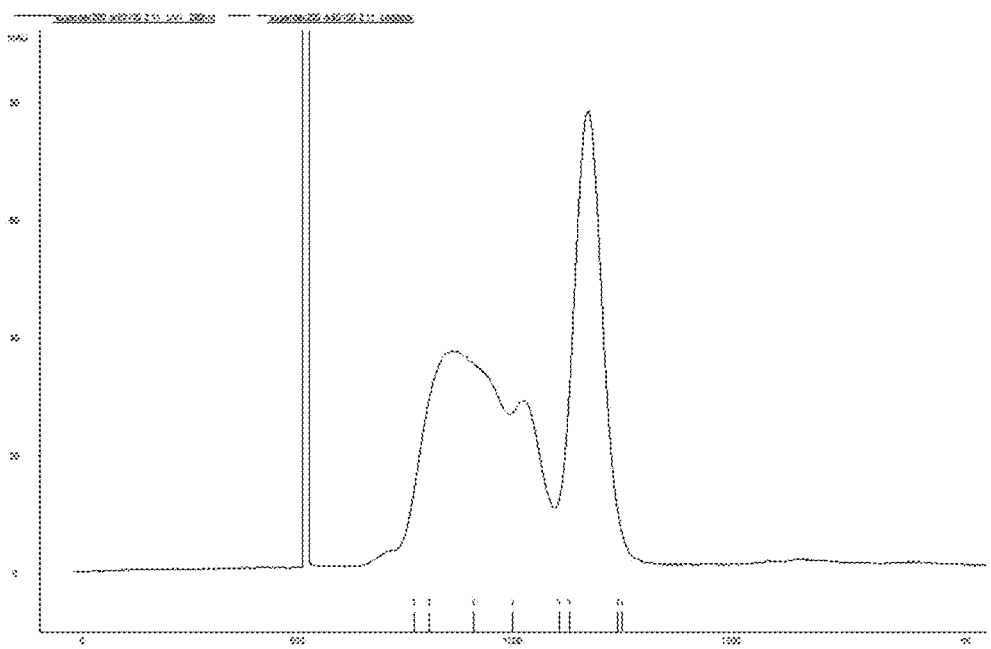
FIG. 9 is a diagram showing the fine purification of fusion protein according to the present invention.

3. Further separation and purification by gel chromatography (FIG. 9)

Column Parameters:

| Packing | Superdex200 |
| --- | --- |
| Column | XK50/60 |
| Column height (cm) | 58 |
| Cross-sectional area of column (cm²) | 19.62 |
| Packing volume (mL) | 1138 |
| Flow rate | mL/min |
| Loading | 1-10% loading volume |

(1) The sterilization was first performed with 300 mL of 0.5 M NaOH at a flow rate of 10 mL/min, and rinsed with ultrapure water to about neutral.

(2) The column was equilibrated with a PBS buffer, pH 7.4, the equilibrium volume was about 1500 mL, and the flow rate was 10 mL/min.

(3) Loading: the sample was a protein A eluent, and the loading volume was 40 mL.

(4) The sample was collected, peak 3 was the target protein peak, for the collection of peak 3, collection was started at onset 10 mAu peak and stopped at post-peak 10 mAu.

(5) Finally, the column was stored with 0.1 M NaOH and the flow rate is 10 mL/min.

Figure 10:
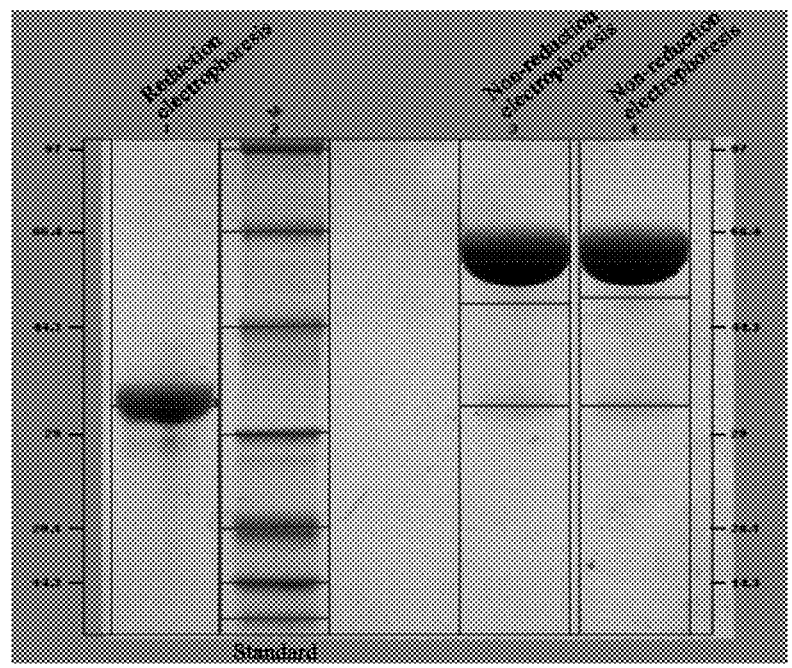
FIG. 10 is a diagram showing the results of analysis of a fusion protein sample by a SDS-PAGE method according to the present invention.
Figure 11:
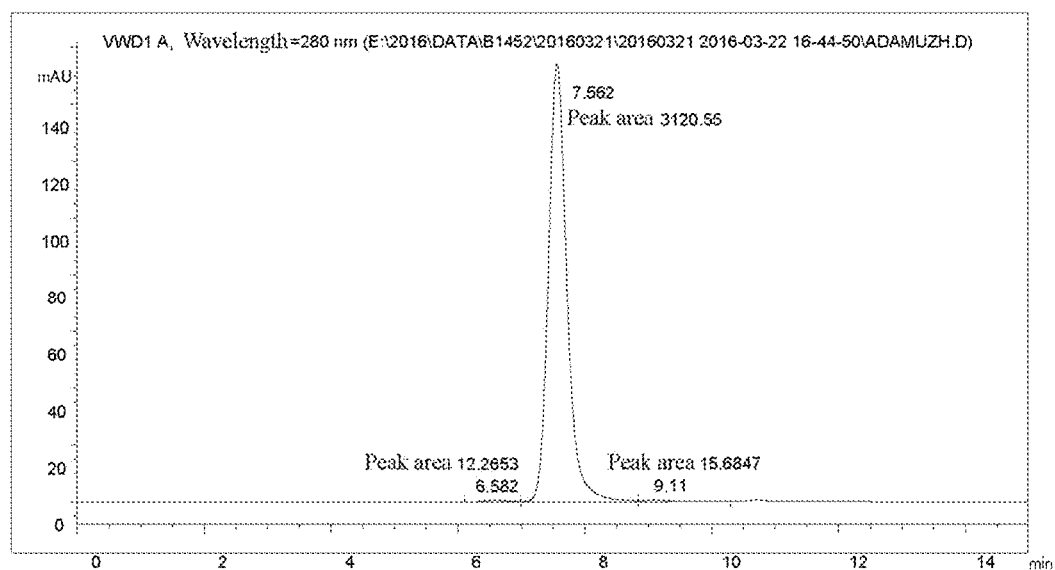
FIG. 11 is a diagram showing the results of analysis of a fusion protein sample by HPLC according to the present invention.

(6) Ultrafiltration concentration of sample: the samples of peak 3 were combined and subjected to ultrafiltration concentration. A 10 kDa ultrafiltration membrane was selected, and the sample was concentrated to a target protein concentration of more than 5 mg/mL, and then the sample was charged and stored in a refrigerator at −80° C. The initial concentration was about 0.29 mg/mL, and the sample was finally concentrated to 27 mL, and the concentration was about 5.53 mg/mL; the sample was charged and cryopreserved. At the same time, samples were subjected to release testing by SDS-PAGE and HPLC (FIG. 10 and FIG. 11), and then used for druggability evaluation studies.

Example 2

Inhibitory Effect of Fusion Protein on Proliferation of Various Tumor Cells

The MTT assay was used to detect the inhibitory effect of the integrin blocker fusion protein obtained in Example 1 on the proliferation of various tumor cells, including melanoma cell B16F10, gastric cancer cell MGC-803, lung cancer cell A549, liver cancer cell Hep-G2, breast cancer cell MDA-MB-231, colon cancer cell HCT-116, human glioma U87, and cervical cancer cell Hela.

The tumor cells were cultured in a 5% $CO_2$ incubator at 37° C. to a density of 90% or more, and collected by trypsinization. The cells were resuspended in the culture liquid and counted under a microscope. The cell concentration was adjusted to $3.0 \times 10^4$ cells/mL. The cell suspension was inoculated into a 96-well plate at 100 μL per well and cultured overnight in a 5% $CO_2$ incubator at 37° C. The fusion proteins I, II, III, IV, V, and the positive drug Taxol were diluted with the culture liquid to respective predetermined concentrations. After the cells were fully adhered, each dilution was added to a 96-well plate at 100 μL per well, respectively. The integrin blocker fusion proteins I, II, III, IV, and V were added as an administration group, Taxol was used as a positive control group, and the culture liquid without any drug was used as a blank control group, and incubated in a 5% $CO_2$ incubator at 37° C. for 48 hours. 20 μL of 5 mg/mL MTT was added to each well of a 96-well plate, and incubation was continued for 4 hours. The medium was aspirated and 100 μL of DMSO per well were added to dissolve. The absorbance was measured at 570 nm with a microplate reader with a reference wavelength of 630 nm, and the proliferation inhibition (PI) was calculated. The formula is as follows:

$$PI(\%) = 1 - \frac{N_{test}}{N_{control}} \times 100\%$$

where $N_{test}$ is the OD value of the test group and $N_{control}$ is the OD value of the blank control group.

Data Statistics:

The test was repeated 5 times independently. The results obtained from the test were calculated as mean±SD, and statistical t-test was performed. P<0.05 was considered as a significant difference, and P<0.01 was considered as an extremely significant difference. The experimental results are shown in Tables 1-8.

TABLE 1

Inhibitory effect of fusion protein I, protein II, protein III, protein IV and protein V on proliferation of melanoma cell line B16F10

| Group (n = 5) | Dose (μg/mL) | A570 nm/A630 nm | PI (%) |
|---|---|---|---|
| Protein I | 1 | 1.0974 ± 0.0157 | 12.47% |
| | 2 | 1.0013 ± 0.0781 | 20.13% |
| | 4 | 0.8603 ± 0.0640* | 31.38% |
| | 8 | 0.6959 ± 0.0419** | 44.49% |
| | 16 | 0.5221 ± 0.0778** | 58.36% |
| | 32 | 0.4330 ± 0.0579** | 65.46% |
| | 64 | 0.3029 ± 0.0286** | 75.84% |
| | 128 | 0.1942 ± 0.0450** | 84.51% |
| | 256 | 0.0817 ± 0.0301** | 93.48% |
| Protein II | 1 | 1.1137 ± 0.0370 | 11.17% |
| | 2 | 1.0250 ± 0.0230 | 18.24% |
| | 4 | 0.8986 ± 0.0731* | 28.32% |
| | 8 | 0.7243 ± 0.0421** | 42.23% |
| | 16 | 0.6400 ± 0.0661** | 48.95% |
| | 32 | 0.5034 ± 0.0286** | 59.85% |
| | 64 | 0.3867 ± 0.0195** | 69.16% |
| | 128 | 0.293 5 ± 0.0313** | 76.59% |
| | 256 | 0.1777 ± 0.0212** | 85.83% |
| Protein III | 1 | 1.1086 ± 0.0151 | 11.57% |
| | 2 | 1.0009 ± 0.0772 | 20.16% |
| | 4 | 0.8592 ± 0.0637* | 31.47% |
| | 8 | 0.6961 ± 0.0412** | 44.48% |
| | 16 | 0.5219 ± 0.0775** | 58.37% |
| | 32 | 0.4327 ± 0.0579** | 65.49% |
| | 64 | 0.3029 ± 0.0284** | 75.84% |
| | 128 | 0.1944 ± 0.0493** | 84.49% |
| | 256 | 0.0818 ± 0.0302** | 93.48% |
| Protein IV | 1 | 1.1128 ± 0.0377 | 11.24% |
| | 2 | 1.0241 ± 0.0233 | 18.31% |
| | 4 | 0.8977 ± 0.0734* | 28.40% |
| | 8 | 0.7234 ± 0.0428** | 42.30% |
| | 16 | 0.6401 ± 0.0668** | 48.94% |
| | 32 | 0.5025 ± 0.0293** | 59.92% |
| | 64 | 0.3858 ± 0.0202** | 69.23% |
| | 128 | 0.2925 ± 0.0320** | 76.67% |
| | 256 | 0.1768 ± 0.0219** | 85.90% |
| Protein V | 1 | 1.1130 ± 0.0372 | 11.22% |
| | 2 | 1.0243 ± 0.0228 | 18.30% |
| | 4 | 0.8979 ± 0.0729* | 28.38% |
| | 8 | 0.7236 ± 0.0423** | 42.28% |
| | 16 | 0.6403 ± 0.0663** | 48.93% |
| | 32 | 0.5027 ± 0.0288** | 59.90% |
| | 64 | 0.3860 ± 0.0197** | 69.21% |
| | 128 | 0.2927 ± 0.0315** | 76.65% |
| | 256 | 0.1770 ± 0.0214** | 85.88% |
| Taxol control | 5 | 0.5996 ± 0.0139** | 52.15% |
| | — | 1.2537 ± 0.0418 | 0.00% |

*P < 0.05,
**P < 0.01 vs control.

The results showed that fusion protein I, protein II, protein III, protein IV and protein V could effectively inhibit melanoma cell line B16F10, and the inhibition rate reached 40% or more at a concentration of 8 μg/mL.

TABLE 2

Inhibitory effect of fusion protein I, protein II, protein III, protein IV and protein V on proliferation of gastric cancer cell MGC-803

| Group (n = 5) | Dose (μg/mL) | A570 nm/A630 nm | PI (%) |
|---|---|---|---|
| Protein I | 1 | 1.1091 ± 0.0439 | 9.23% |
| | 2 | 1.0111 ± 0.0376* | 17.25% |
| | 4 | 0.8768 ± 0.0417 | 28.24% |
| | 8 | 0.7121 ± 0.0373* | 41.72% |
| | 16 | 0.5439 ± 0.0265** | 55.49% |
| | 32 | 0.4426 ± 0.0382** | 63.78% |
| | 64 | 0.3216 ± 0.0331** | 73.68% |
| | 128 | 0.2016 ± 0.0217** | 83.50% |
| | 256 | 0.1023 ± 0.0231** | 91.63% |
| Protein II | 1 | 1.1122 ± 0.0374 | 8.98% |
| | 2 | 1.0149 ± 0.0253 | 16.94% |
| | 4 | 0.8231 ± 0.0396* | 32.64% |
| | 8 | 0.7231 ± 0.0215* | 40.82% |
| | 16 | 0.5216 ± 0.0192** | 57.31% |
| | 32 | 0.4398 ± 0.0347** | 64.01% |
| | 64 | 0.3378 ± 0.0286** | 72.35% |
| | 128 | 0.2203 ± 0.0147** | 81.97% |
| | 256 | 0.0987 ± 0.0159** | 91.92% |
| Protein III | 1 | 1.1084 ± 0.0332 | 9.29% |
| | 2 | 1.1077 ± 0.0292 | 9.35% |
| | 4 | 0.8854 ± 0.0273* | 27.54% |
| | 8 | 0.7222 ± 0.0316 | 40.90% |
| | 16 | 0.5254 ± 0.0198** | 57.00% |
| | 32 | 0.4285 ± 0.0249** | 64.93% |
| | 64 | 0.3269 ± 0.0217** | 73.25% |
| | 128 | 0.2089 ± 0.0206** | 82.90% |
| | 256 | 0.0999 ± 0.0193** | 91.82% |
| Protein IV | 1 | 1.1201 ± 0.0432 | 8.33% |
| | 2 | 1.1181 ± 0.0385 | 8.49% |
| | 4 | 0.890 ± 0.0362* | 27.16% |
| | 8 | 0.7213 ± 0.0319* | 40.97% |
| | 16 | 0.5345 ± 0.0297** | 56.26% |
| | 32 | 0.4198 ± 0.0255** | 65.64% |
| | 64 | 0.3169 ± 0.0213** | 74.06% |
| | 128 | 0.2211 ± 0.0198** | 81.91% |
| | 256 | 0.0970 ± 0.0203** | 92.06% |
| Protein V | 1 | 1.1075 ± 0.0402 | 9.36% |
| | 2 | 1.1062 ± 0.0299 | 9.47% |
| | 4 | 0.8868 ± 0.0342* | 27.42% |
| | 8 | 0.7302 ± 0.0245* | 40.24% |
| | 16 | 0.5164 ± 0.0197* | 57.74% |
| | 32 | 0.4333 ± 0.0218** | 64.54% |
| | 64 | 0.3388 ± 0.0324** | 72.27% |
| | 128 | 0.2099 ± 0.0310** | 82.82% |
| | 256 | 0.0862 ± 0.0293** | 92.95% |
| Taxol control | 5 | 0.6011 ± 0.0148 | 50.81% |
| | — | 1.2219 | 0.00% |

*P < 0.05,
**P < 0.01 vs control.

The results showed that fusion protein I, protein II, protein III, protein IV and protein V could effectively inhibit gastric cancer cell MGC-803, and the inhibition rate reached about 40% at a concentration of 8 μg/mL.

TABLE 3

Inhibitory effect of fusion protein I, protein II, protein III, protein IV and protein V on proliferation of lung cancer cell A549

| Group (n = 5) | Dose (μg/mL) | A570 nm/A630 nm | PI (%) |
|---|---|---|---|
| Protein I | 1 | 0.9036 ± 0.0441 | 6.72% |
| | 2 | 0.8409 ± 0.0378 | 13.19% |
| | 4 | 0.7865 ± 0.0417* | 18.81% |
| | 8 | 0.6665 ± 0.0373 | 31.20% |
| | 16 | 0.5789 ± 0.0267* | 40.24% |
| | 32 | 0.4687 ± 0.0384** | 51.62% |
| | 64 | 0.3323 ± 0.0333** | 65.70% |
| | 128 | 0.1745 ± 0.0219** | 81.99% |
| | 256 | 0.0896 ± 0.0233** | 90.75% |
| Protein II | 1 | 0.8885 ± 0.0374 | 8.28% |
| | 2 | 0.7933 ± 0.0253 | 18.11% |
| | 4 | 0.7005 ± 0.0396 | 27.69% |
| | 8 | 0.6325 ± 0.0215* | 34.71% |
| | 16 | 0.5923 ± 0.0192** | 38.86% |
| | 32 | 0.5006 ± 0.0347** | 48.32% |
| | 64 | 0.4106 ± 0.0286** | 57.61% |

TABLE 3-continued

Inhibitory effect of fusion protein I, protein II, protein III, protein IV and protein V on proliferation of lung cancer cell A549

| Group (n = 5) | Dose (μg/mL) | A570 nm/A630 nm | PI (%) |
|---|---|---|---|
| | 128 | 0.2008 ± 0.0147** | 79.27% |
| | 256 | 0.1165 ± 0.0159** | 87.97% |
| Protein III | 1 | 0.9105 ± 0.0332 | 6.01% |
| | 2 | 0.8560 ± 0.0292 | 11.63% |
| | 4 | 0.7769 ± 0.0273* | 19.80% |
| | 8 | 0.6949 ± 0.0316 | 28.26% |
| | 16 | 0.5897 ± 0.0198 | 39.12% |
| | 32 | 0.4436 ± 0.0249* | 54.21% |
| | 64 | 0.3165 ± 0.0217** | 67.33% |
| | 128 | 0.2116 ± 0.0206** | 78.16% |
| | 256 | 0.1212 ± 0.0195** | 87.49% |
| Protein IV | 1 | 0.8992 ± 0.0434 | 7.17% |
| | 2 | 0.8690 ± 0.0385 | 10.29% |
| | 4 | 0.7613 ± 0.0364* | 21.41% |
| | 8 | 0.6796 ± 0.0321* | 29.84% |
| | 16 | 0.5993 ± 0.0299** | 38.13% |
| | 32 | 0.434 ± 0.0257** | 55.20% |
| | 64 | 0.3396 ± 0.0215** | 64.94% |
| | 128 | 0.2398 ± 0.0200** | 75.25% |
| | 256 | 0.1331 ± 0.0205** | 86.26% |
| Protein V | 1 | 0.8911 ± 0.0404 | 8.01% |
| | 2 | 0.8599 ± 0.0301 | 11.23% |
| | 4 | 0.7439 ± 0.0344* | 23.21% |
| | 8 | 0.6632 ± 0.0247 | 31.54% |
| | 16 | 0.5555 ± 0.0199* | 42.66% |
| | 32 | 0.4488 ± 0.0220** | 53.67% |
| | 64 | 0.3489 ± 0.0326** | 63.98% |
| | 128 | 0.2249 ± 0.0312** | 76.78% |
| | 256 | 0.1029 ± 0.0295** | 89.38% |
| Taxol control | 5 | 0.4269 | 55.93% |
| | — | 0.9687 | 0.00% |

*P < 0.05,
**P < 0.01 vs control.

The results showed that fusion protein I, protein II, protein III, protein IV and protein V could effectively inhibit lung cancer cell A549, and the inhibition rate reached about 40% at a concentration of 16 μg/mL.

TABLE 4

Inhibitory effect of fusion protein I, protein II, protein III, protein IV and protein V on proliferation of liver cancer cell Hep-G2

| Group (n = 5) | Dose (μg/mL) | A570 nm/A630 nm | PI (%) |
|---|---|---|---|
| Protein I | 1 | 0.6669 ± 0.0428 | 2.61% |
| | 2 | 0.6009 ± 0.0362 | 12.25% |
| | 4 | 0.5879 ± 0.0404 | 14.15% |
| | 8 | 0.5555 ± 0.0373 | 18.88% |
| | 16 | 0.5220 ± 0.0259 | 23.77% |
| | 32 | 0.4862 ± 0.0330 | 29.00% |
| | 64 | 0.4397 ± 0.0327 | 35.79% |
| | 128 | 0.3836 ± 0.0218 | 43.98% |
| | 256 | 0.3223 ± 0.0233 | 52.94% |
| Protein II | 1 | 0.6746 ± 0.0372 | 1.49% |
| | 2 | 0.6132 ± 0.0253 | 10.46% |
| | 4 | 0.5799 ± 0.0396 | 15.32% |
| | 8 | 0.5499 ± 0.0215 | 19.70% |
| | 16 | 0.5190 ± 0.0185 | 24.21% |
| | 32 | 0.4706 ± 0.0374 | 31.28% |
| | 64 | 0.4256 ± 0.0268 | 37.85% |
| | 128 | 0.3801 ± 0.0174 | 44.49% |
| | 256 | 0.3156 ± 0.0151 | 53.91% |
| Protein III | 1 | 0.6726 ± 0.0335 | 1.78% |
| | 2 | 0.6111 ± 0.0287 | 10.76% |
| | 4 | 0.5862 ± 0.0275 | 14.40% |
| | 8 | 0.5586 ± 0.0105 | 18.43% |
| | 16 | 0.5102 ± 0.0214 | 25.50% |
| | 32 | 0.4756 ± 0.0245 | 30.55% |
| | 64 | 0.4213 ± 0.0219 | 38.48% |
| | 128 | 0.3786 ± 0.0214 | 44.71% |
| | 256 | 0.3259 ± 0.0194 | 52.41% |

TABLE 4-continued

Inhibitory effect of fusion protein I, protein II, protein III, protein IV and protein V on proliferation of liver cancer cell Hep-G2

| Group (n = 5) | Dose (μg/mL) | A570 nm/A630 nm | PI (%) |
|---|---|---|---|
| Protein IV | 1 | 0.6656 ± 0.0194 | 2.80% |
| | 2 | 0.6232 ± 0.0380 | 9.00% |
| | 4 | 0.5899 ± 0.0369 | 13.86% |
| | 8 | 0.5578 ± 0.0357 | 18.55% |
| | 16 | 0.4966 ± 0.0284 | 27.48% |
| | 32 | 0.4486 ± 0.0253 | 34.49% |
| | 64 | 0.4006 ± 0.0214 | 41.50% |
| | 128 | 0.3698 ± 0.0203 | 46.00% |
| | 256 | 0.3111 ± 0.0206 | 54.57% |
| Protein V | 1 | 0.6700 ± 0.0419 | 2.16% |
| | 2 | 0.6213 ± 0.0322 | 9.27% |
| | 4 | 0.5910 ± 0.0341 | 13.70% |
| | 8 | 0.5601 ± 0.0247 | 18.21% |
| | 16 | 0.5056 ± 0.0199 | 26.17% |
| | 32 | 0.4578 ± 0.0217 | 33.15% |
| | 64 | 0.4005 ± 0.0323 | 41.52% |
| | 128 | 0.3613 ± 0.0308 | 47.24% |
| | 256 | 0.3017 ± 0.0297 | 55.95% |
| Taxol control | 5 | 0.3258 | 52.42% |
| | — | 0.6848 | 0.00% |

* P < 0.05,
**P < 0.01 vs control.

The results showed that fusion protein I, protein II, protein III, protein IV and protein V had a certain inhibitory effect on liver cancer cell Hep-G2, and the inhibition rate increased with the increase of concentration.

TABLE 5

Inhibitory effect of fusion protein I, protein II, protein III, protein IV and protein V on proliferation of breast cancer cell MDA-MB-231

| Group (n = 5) | Dose (μg/mL) | A570 nm/A630 nm | PI (%) |
|---|---|---|---|
| Protein I | 1 | 0.9977 ± 0.0403 | 3.96% |
| | 2 | 0.9665 ± 0.0397 | 6.96% |
| | 4 | 0.9201 ± 0.0382 | 11.43% |
| | 8 | 0.8815 ± 0.0410 | 15.14% |
| | 16 | 0.8006 ± 0.0287 | 22.93% |
| | 32 | 0.7586 ± 0.0336 | 26.97% |
| | 64 | 0.6988 ± 0.0296 | 32.73% |
| | 128 | 0.6587 ± 0.0314 | 36.59% |
| | 256 | 0.6023 ± 0.0327 | 42.02% |
| Protein II | 1 | 0.9859 ± 0.0397 | 5.09% |
| | 2 | 0.9552 ± 0.0419 | 8.05% |
| | 4 | 0.9150 ± 0.0283 | 11.92% |
| | 8 | 0.8806 ± 0.0345 | 15.23% |
| | 16 | 0.8110 ± 0.0298 | 21.93% |
| | 32 | 0.7546 ± 0.0274 | 27.36% |
| | 64 | 0.6945 ± 0.0326 | 33.14% |
| | 128 | 0.6589 ± 0.0287 | 36.57% |
| | 256 | 0.6012 ± 0.0311 | 42.13% |
| Protein III | 1 | 0.9913 ± 0.0412 | 4.57% |
| | 2 | 0.9663 ± 0.0392 | 6.98% |
| | 4 | 0.9103 ± 0.0387 | 12.37% |
| | 8 | 0.8714 ± 0.0354 | 16.11% |
| | 16 | 0.7956 ± 0.0291 | 23.41% |
| | 32 | 0.7601 ± 0.0275 | 26.83% |
| | 64 | 0.6963 ± 0.0211 | 32.97% |
| | 128 | 0.6613 ± 0.0255 | 36.34% |
| | 256 | 0.6213 ± 0.0230 | 40.19% |
| Protein IV | 1 | 0.9905 ± 0.0413 | 4.65% |
| | 2 | 0.9642 ± 0.0409 | 7.18% |
| | 4 | 0.9203 ± 0.0385 | 11.41% |
| | 8 | 0.8756 ± 0.0396 | 15.71% |
| | 16 | 0.7988 ± 0.0358 | 23.10% |
| | 32 | 0.7585 ± 0.0312 | 26.98% |
| | 64 | 0.6946 ± 0.0292 | 33.13% |
| | 128 | 0.6425 ± 0.0300 | 38.15% |
| | 256 | 0.6003 ± 0.0275 | 42.21% |
| Protein V | 1 | 0.9868 ± 0.03972 | 5.01% |
| | 2 | 0.9505 ± 0.0337 | 8.50% |

TABLE 5-continued

Inhibitory effect of fusion protein I, protein II, protein III, protein IV and protein V on proliferation of breast cancer cell MDA-MB-231

| Group (n = 5) | Dose (µg/mL) | A570 nm/A630 nm | PI (%) |
|---|---|---|---|
| | 4 | 0.9103 ± 0.0358 | 12.37% |
| | 8 | 0.8789 ± 0.03131 | 15.39% |
| | 16 | 0.7968 ± 0.0299 | 23.30% |
| | 32 | 0.7546 ± 0.0234 | 27.36% |
| | 64 | 0.6988 ± 0.0216 | 32.73% |
| | 128 | 0.6431 ± 0.0225 | 38.09% |
| | 256 | 0.6100 ± 0.0199 | 41.28% |
| Taxol | 5 | 0.4156 ± 0.0287 | 59.99% |
| control | — | 1.0388 ± 0.054 | 0.00% |

\* $P < 0.05$,
\*\*$P < 0.01$ vs control.

The results showed that fusion protein I, protein II, protein III, protein IV and protein V could effectively inhibit breast cancer cell line MDA-MB-231, and the inhibition rate reached 40% or more at a concentration of 256 µg/mL.

TABLE 6

Inhibitory effect of fusion protein I, protein II, protein III, protein IV and protein V on proliferation of colon cancer cells HCT-116

| Group (n = 5) | Dose (µg/mL) | A570 nm/A630 nm | PI (%) |
|---|---|---|---|
| Protein I | 1 | 0.8205 ± 0.0411 | 6.78% |
| | 2 | 0.7859 ± 0.0382 | 10.71% |
| | 4 | 0.7587 ± 0.0371 | 13.80% |
| | 8 | 0.7110 ± 0.0413 | 19.22% |
| | 16 | 0.6778 ± 0.0285 | 22.99% |
| | 32 | 0.6114 ± 0.0331 | 30.54% |
| | 64 | 0.5468 ± 0.0296 | 37.88% |
| | 128 | 0.4988 ± 0.0315 | 43.33% |
| | 256 | 0.4458 ± 0.0324 | 49.35% |
| Protein II | 1 | 0.8310 ± 0.0394 | 5.59% |
| | 2 | 0.7925 ± 0.0415 | 9.96% |
| | 4 | 0.7555 ± 0.0283 | 14.17% |
| | 8 | 0.7023 ± 0.0347 | 20.21% |
| | 16 | 0.6556 ± 0.0292 | 25.52% |
| | 32 | 0.6113 ± 0.0279 | 30.55% |
| | 64 | 0.5498 ± 0.0374 | 37.54% |
| | 128 | 0.4898 ± 0.0289 | 44.35% |
| | 256 | 0.4497 ± 0.0316 | 48.91% |
| Protein III | 1 | 0.8333 ± 0.0414 | 5.33% |
| | 2 | 0.7964 ± 0.0397 | 9.52% |
| | 4 | 0.7623 ± 0.0382 | 13.39% |
| | 8 | 0.7022 ± 0.0351 | 20.22% |
| | 16 | 0.6663 ± 0.0298 | 24.30% |
| | 32 | 0.6023 ± 0.0276 | 31.57% |
| | 64 | 0.5557 ± 0.0219 | 36.87% |
| | 128 | 0.4878 ± 0.0253 | 44.58% |
| | 256 | 0.4502 ± 0.0238 | 48.85% |
| Protein IV | 1 | 0.823 ± 0.0412 | 6.50% |
| | 2 | 0.7878 ± 0.0401 | 10.50% |
| | 4 | 0.7544 ± 0.0382 | 14.29% |
| | 8 | 0.7101 ± 0.0390 | 19.33% |
| | 16 | 0.6787 ± 0.0353 | 22.89% |
| | 32 | 0.6135 ± 0.0312 | 30.30% |
| | 64 | 0.5654 ± 0.0299 | 35.76% |
| | 128 | 0.4879 ± 0.0305 | 44.57% |
| | 256 | 0.4421 ± 0.0271 | 49.77% |
| Protein V | 1 | 0.8256 ± 0.0392 | 6.20% |
| | 2 | 0.7811 ± 0.0333 | 11.26% |
| | 4 | 0.7333 ± 0.0352 | 16.69% |
| | 8 | 0.7113 ± 0.0311 | 19.19% |
| | 16 | 0.6798 ± 0.0283 | 22.77% |
| | 32 | 0.6154 ± 0.0236 | 30.08% |
| | 64 | 0.5582 ± 0.0210 | 36.58% |
| | 128 | 0.4888 ± 0.0227 | 44.47% |
| | 256 | 0.4411 ± 0.0196 | 49.89% |
| Taxol | 5 | 0.4103 ± 0.0287 | 53.39% |
| control | — | 0.8802 ± 0.0536 | 00.00% |

\* $P < 0.05$,
\*\*$P < 0.01$ vs control.

The results showed that fusion protein I, protein II, protein III, protein IV and protein V could effectively inhibit colon cancer cell HCT-116, and the inhibition rate reached 40% or more at a concentration of 128 µg/mL.

TABLE 7

Inhibitory effect of fusion protein I, protein II, protein III, protein IV and protein V on proliferation of human glioma U87

| Group (n = 5) | Dose (µg/mL) | A570 nm/A630 nm | PI(%) |
|---|---|---|---|
| Protein I | 1 | 0.6805 ± 0.0403 | 2.77% |
| | 2 | 0.658 ± 0.0377 | 5.99% |
| | 4 | 0.6102 ± 0.0324 | 12.82% |
| | 8 | 0.5521 ± 0.0403 | 21.12% |
| | 16 | 0.5120 ± 0.0275 | 26.85% |
| | 32 | 0.4612 ± 0.0361 | 34.10% |
| | 64 | 0.3833 ± 0.0266 | 45.24% |
| | 128 | 0.2921 ± 0.0345 | 58.27% |
| | 256 | 0.2113 ± 0.0374 | 69.81% |
| Protein II | 1 | 0.6788 ± 0.0374 | 3.01% |
| | 2 | 0.6523 ± 0.0405 | 6.80% |
| | 4 | 0.6021 ± 0.0233 | 13.97% |
| | 8 | 0.5423 ± 0.0357 | 22.52% |
| | 16 | 0.5006 ± 0.0282 | 28.48% |
| | 32 | 0.4652 ± 0.0249 | 33.53% |
| | 64 | 0.4080 ± 0.0366 | 41.71% |
| | 128 | 0.3143 ± 0.0279 | 55.09% |
| | 256 | 0.2222 ± 0.0316 | 68.25% |
| Protein III | 1 | 0.6923 ± 0.0424 | 1.09% |
| | 2 | 0.6655 ± 0.0327 | 4.91% |
| | 4 | 0.6132 ± 0.0372 | 12.39% |
| | 8 | 0.5461 ± 0.0341 | 21.97% |
| | 16 | 0.5012 ± 0.0218 | 28.39% |
| | 32 | 0.4589 ± 0.0256 | 34.43% |
| | 64 | 0.3520 ± 0.0219 | 49.71% |
| | 128 | 0.2465 ± 0.0253 | 64.78% |
| | 256 | 0.1989 ± 0.0208 | 71.58% |
| Protein IV | 1 | 0.6887 ± 0.0432 | 1.60% |
| | 2 | 0.6531 ± 0.0391 | 6.69% |
| | 4 | 0.6154 ± 0.0352 | 12.07% |
| | 8 | 0.5471 ± 0.0360 | 21.83% |
| | 16 | 0.5078 ± 0.0383 | 27.45% |
| | 32 | 0.4602 ± 0.0322 | 34.25% |
| | 64 | 0.3623 ± 0.0229 | 48.24% |
| | 128 | 0.2755 ± 0.0305 | 60.64% |
| | 256 | 0.2057 ± 0.0251 | 70.61% |
| Protein V | 1 | 0.6822 ± 0.0372 | 2.53% |
| | 2 | 0.6577 ± 0.0373 | 6.03% |
| | 4 | 0.6189 ± 0.0382 | 11.57% |
| | 8 | 0.5579 ± 0.0331 | 20.29% |
| | 16 | 0.5111 ± 0.0299 | 26.98% |
| | 32 | 0.4658 ± 0.0246 | 33.45% |
| | 64 | 0.3687 ± 0.0260 | 47.32% |
| | 128 | 0.2741 ± 0.0257 | 60.84% |
| | 256 | 0.2155 ± 0.0196 | 69.21% |
| Taxol | 5 | 0.2177 ± 0.0277 | 68.90% |
| control | — | 0.6999 ± 0.0572 | 00.00% |

\* $P < 0.05$,
\*\*$P < 0.01$ vs control.

The results showed that fusion protein I, protein II, protein III, protein IV, and protein V could significantly inhibit human glioma U87, and the inhibition rate reached about 50% at a concentration of 64 µg/mL.

TABLE 8

Inhibitory effect of fusion protein I, protein II, protein III, protein IV and protein V on proliferation of cervical cancer cell Hela

| Group (n = 5) | Dose (μg/mL) | A570 nm/A630 nm | PI (%) |
|---|---|---|---|
| Protein I | 1 | 0.7882 ± 0.0412 | 1.38% |
| | 2 | 0.7454 ± 0.0374 | 6.73% |
| | 4 | 0.6879 ± 0.0381 | 13.93% |
| | 8 | 0.6135 ± 0.0362 | 23.24% |
| | 16 | 0.5365 ± 0.0293 | 32.87% |
| | 32 | 0.4587 ± 0.0325 | 42.61% |
| | 64 | 0.3878 ± 0.0287 | 51.48% |
| | 128 | 0.2655 ± 0.0302 | 66.78% |
| | 256 | 0.1522 ± 0.0315 | 80.96% |
| Protein II | 1 | 0.7798 ± 0.0386 | 2.43% |
| | 2 | 0.7412 ± 0.0407 | 7.26% |
| | 4 | 0.6946 ± 0.0272 | 13.09% |
| | 8 | 0.6312 ± 0.0313 | 21.02% |
| | 16 | 0.5418 ± 0.0286 | 32.21% |
| | 32 | 0.4788 ± 0.0262 | 40.09% |
| | 64 | 0.4023 ± 0.0314 | 49.66% |
| | 128 | 0.2878 ± 0.0275 | 63.99% |
| | 256 | 0.1748 ± 0.0303 | 78.13% |
| Protein III | 1 | 0.7806 ± 0.0400 | 2.33% |
| | 2 | 0.7465 ± 0.0381 | 6.59% |
| | 4 | 0.6888 ± 0.0374 | 13.81% |
| | 8 | 0.6254 ± 0.0342 | 21.75% |
| | 16 | 0.5478 ± 0.0279 | 31.46% |
| | 32 | 0.4825 ± 0.0263 | 39.63% |
| | 64 | 0.4121 ± 0.0199 | 48.44% |
| | 128 | 0.3022 ± 0.0242 | 62.19% |
| | 256 | 0.1879 ± 0.0228 | 76.49% |
| Protein IV | 1 | 0.7856 ± 0.0401 | 1.70% |
| | 2 | 0.7512 ± 0.0397 | 6.01% |
| | 4 | 0.7012 ± 0.0373 | 12.26% |
| | 8 | 0.6313 ± 0.0384 | 21.01% |
| | 16 | 0.5571 ± 0.0346 | 30.29% |
| | 32 | 0.4922 ± 0.0301 | 38.41% |
| | 64 | 0.4023 ± 0.0279 | 49.66% |
| | 128 | 0.3044 ± 0.0297 | 61.91% |
| | 256 | 0.2016 ± 0.0268 | 74.77% |
| Protein V | 1 | 0.7784 ± 0.0386 | 2.60% |
| | 2 | 0.7354 ± 0.0325 | 7.98% |
| | 4 | 0.6879 ± 0.0346 | 13.93% |
| | 8 | 0.6121 ± 0.0301 | 23.41% |
| | 16 | 0.5346 ± 0.0287 | 33.11% |
| | 32 | 0.4897 ± 0.0222 | 38.73% |
| | 64 | 0.4155 ± 0.0204 | 48.01% |
| | 128 | 0.3111 ± 0.0213 | 61.07% |
| | 256 | 0.2004 ± 0.0182 | 74.92% |
| Taxol | 5 | 0.2114 ± 0.0275 | 73.55% |
| control | — | 0.7992 ± 0.0592 | 0.00% |

\* $P < 0.05$,
\*\* $P < 0.01$ vs control.

The results showed that fusion protein I, protein II, protein III, protein IV, and protein V could significantly inhibit cervical cancer cell Hela, and the inhibition rate reached about 45% at a concentration of 64 μg/mL.

Taken together, the inhibitory effects of fusion protein I, protein II, protein III, protein IV, and protein V integrin blockers on proliferation of various tumor cells are shown in Tables 1-8. The fusion protein can effectively inhibit proliferation of gastric cancer, lung cancer, liver cancer, breast cancer, melanoma, colon cancer, glioma, and cervical cancer. Among them, the inhibition rate of melanoma, gastric cancer and lung cancer reached 50% or more at the concentration of 32 μg/mL; the inhibition rate of glioma and cervical cancer reached 40% or more at the concentration of 64 μg/mL; higher concentrations were required to achieve effective inhibition on colon cancer, liver cancer, and breast cancer cells.

Example 3

Detection of Inhibitory Effects of Fusion Protein I, Protein II, Protein III, Protein IV, and Protein V on Migration of Human Umbilical Vein Endothelial Cells by Three-Dimensional Transwell Assay Human umbilical vein endothelial cells (HUVECs) were cultured with endothelial cell culture fluid containing 5% fetal bovine serum and 1×ECGS in a 5% $CO_2$ incubator at 37° C., to a confluence of 90% or more, and then inhibitory effects of fusion protein I, protein II, protein III, protein IV, and protein V on migration of endothelial cells were detected by transwell assay, in which only endothelial cells HUVEC of passage 2 to 8 were used, and the specific operation was as follows.

(1) 10 mg/mL Matrigel was diluted with a DMEM medium at a ratio of 1:4, coated on a transwell chamber membrane, and air-dried at room temperature.

(2) HUVEC cells cultured to logarithmic phase were digested with 0.2% EDTA, collected, washed twice with PBS, followed by resuspended in an endothelial cell culture liquid containing 0.1% BSA, counted under a microscope, and the cell concentration was adjusted to $1 \times 10^5$ cells/mL;

(3) Test solutions for each group were formulated and diluted to 100 μL with a cell culture liquid containing 0.1% BSA;

Groups were divided as follows:

Blank control group: a cell culture liquid containing no drug;

Endostar group: 5 mg/mL Endostar solution diluted to a predetermined concentration with a cell culture liquid containing no drug;

Fusion protein group: the fusion protein diluted to 10 μg/mL with a cell culture liquid containing no drug.

(4) The cells were inoculated into a transwell chamber at 100 μL per well, and test solutions for each group were added to the chamber. To a 24-well plate, 0.6 mL of endothelial cell culture liquid containing 5% fetal bovine serum and 1×ECGS was added to stimulate cell migration, and incubated at 5% $CO_2$ for 24 h at 37° C.

(5) The culture liquid in the well was discarded. The cells were fixed with 90% alcohol at room temperature for 30 min, stained with 0.1% crystal violet for 10 min at room temperature, and rinsed with water. Un-migrated cells in the upper layer were gently wiped off by a cotton swab. The observation was carried out under microscope and four fields of view were selected for taking photos and counting. The migration inhibition (MI) was calculated according to the formula:

$$MI(\%) = 1 - \frac{N_{test}}{N_{control}} \times 100\%$$

where $N_{test}$ is the migration cell number in the test group, and $N_{control}$ is the migration cell number in the blank control group.

Data Statistics:

The test was repeated 3 times independently. The results obtained from the test were calculated as mean±SD, and statistical t-test was performed. $P < 0.05$ was considered as a significant difference, and $P < 0.01$ was considered as an extremely significant difference. The experimental results are shown in Table 9.

TABLE 9

Migration inhibition of HUVEC by fusion protein I, protein II, protein III, protein IV, and protein V

| Group (n = 5) | Dose (µg/mL) | Migration cell number | MI (%) |
|---|---|---|---|
| Protein I | 0.25 | 2031.0 ± 184.39 | 19.18% |
|  | 0.5 | 1748.5 ± 361.22* | 30.42% |
|  | 1 | 923.0 ± 153.98** | 63.27% |
|  | 2 | 743.0 ± 233.57** | 70.43% |
|  | 4 | 795.0 ± 45.32** | 68.36% |
|  | 8 | 1397.0 ± 176.19* | 44.41% |
| Protein II | 0.25 | 2108.0 ± 75.27 | 16.12% |
|  | 0.5 | 1203.5 ± 220.14** | 52.11% |
|  | 1 | 677.0 ± 24.72** | 73.06% |
|  | 2 | 569.5 ± 270.29** | 77.34% |
|  | 4 | 858.0 ± 145.87** | 65.86% |
|  | 8 | 1762.0 ± 183.97* | 29.88% |
| Protein III | 0.25 | 2139 ± 184.39* | 14.88% |
|  | 0.5 | 1209 ± 307.58** | 51.89% |
|  | 1 | 873 ± 142.04** | 65.26% |
|  | 2 | 752 ± 192.37** | 70.08% |
|  | 4 | 538 ± 54.26** | 78.59% |
|  | 8 | 1420 ± 136.22* | 43.49% |
| Protein IV | 0.25 | 1999 ± 194.25* | 20.45% |
|  | 0.5 | 1456 ± 122.37** | 42.06% |
|  | 1 | 752 ± 87.54** | 70.08% |
|  | 2 | 591 ± 69.28** | 76.48% |
|  | 4 | 647 ± 31.35** | 74.25% |
|  | 8 | 1346 ± 177.36* | 46.44% |
| Protein V | 0.25 | 2058 ± 169.52* | 18.11% |
|  | 0.5 | 1332 ± 84.87** | 47.00% |
|  | 1 | 943 ± 53.96** | 62.48% |
|  | 2 | 533 ± 32.33** | 78.79% |
|  | 4 | 702 ± 64.43** | 72.07% |
|  | 8 | 1139 ± 145.66* | 54.68% |
| Sunitinib | $8.0 \cdot 10^{-6}$ | 449.0 ± 153.86** | 82.13% |
| Control | — | 2513.0 ± 79.16 | 0.00% |

*P < 0.05,
**P < 0.01 vs control

As seen from the experimental results, under the action of fusion protein I, protein II, protein III, protein IV and protein V, the number of migrated endothelial cells was significantly reduced compared with that of the negative control, and the migration inhibition of HUVEC was significant at the concentration of 2 µg/mL. The inhibition rate was 70% or more, and the inhibition rate on cell migration was extremely significant compared with that of the negative control (P<0.01). Between 0.5 µg/mL and 4 µg/mL, the best inhibitory effect was achieved.

Example 4

Effect of Fusion Protein I, Protein II, Protein III, Protein IV and Protein V on Proliferation of Mouse Spleen Lymphocytes The spleen of a mouse was taken out under sterile conditions, washed 3 times with empty 1640 medium, ground in 5 mL syringe core, filtered through a 200-mesh sieve, and prepared into a single cell suspension, the single cell suspension was centrifuged (1000 rpm, 5 min), and the supernatant was discarded. Tris-NH$_4$Cl was used to break the red blood cells, which were allowed to stand in an ice water bath for 4 min and centrifuged (1000 rpm, 5 min), the supernatant was discarded, and the cells were washed twice with sterile PBS. Finally, cells were suspended in a 10% fetal calf serum RPMI 1640 culture liquid (5 mL), counted, adjusted to a cell concentration of 5×10$^6$ cells/mL, and cultured in a 96-well culture plate.

The experiment comprises, a blank control group, a concanavalin A (ConA) group, a dexamethasone (Dex) group (0.02 mg/mL), and protein A and protein G used as experimental groups. After each group was added with spleen lymphocyte suspension, 100 µL per well, the blank control group was added with 100 µL of empty 1640 culture liquid, ConA group was added with ConA (final concentration of 5 µg/mL), and Dex group was added with Dex, and protein A and protein G were added with ConA (final concentration of 5 µg/mL) on the basis of addition of different concentrations of extracts. The cells were statically cultured in a cell incubator at 37° C. for 48 h. After the completion of the culture, 20 µL of MTT was added to each well, and the culture was continued for 4 h. Finally, all the solutions in each well were discarded, 100 µL of DMSO was added to each well, and the mixture was shaken and detected by a microplate reader for OD value at 570 nm. 5 parallels were preformed for per well. The experimental results are shown in Table 10.

TABLE 10

Effect of fusion protein I, protein II, protein III, protein IV, protein V on the proliferation of mouse spleen lymphocytes

| Group (n = 5) | Dose (µg/mL) | A570 nm/A630 nm | PI (%) |
|---|---|---|---|
| Protein I | 8 | 0.5412 ± 0.0231 | 7.80% |
|  | 32 | 0.4733 ± 0.0194* | 19.37% |
|  | 128 | 0.3726 ± 0.0208** | 28.21% |
| Protein II | 8 | 0.5514 ± 0.0187 | 6.84% |
|  | 32 | 0.4637 ± 0.0155* | 21.66% |
|  | 128 | 0.3825 ± 0.0103** | 35.38% |
| Protein III | 8 | 0.5618 ± 0.0169 | 5.09% |
|  | 32 | 0.4827 ± 0.0103* | 18.45% |
|  | 128 | 0.3746 ± 0.0874** | 27.82% |
| Protein IV | 8 | 0.5603 ± 0.0258 | 5.34% |
|  | 32 | 0.4936 ± 0.0903* | 16.61% |
|  | 128 | 0.3949 ± 0.0121** | 33.28% |
| Protein V | 8 | 0.5492 ± 0.0111 | 7.21% |
|  | 32 | 0.4836 ± 0.0302* | 18.30% |
|  | 128 | 0.3942 ± 0.0183** | 33.40% |
| ConA | — | 0.6033 ± 0.0341 | — |
| Dex | 20 | 0.3401 ± 0.1131** | 41.19% |
| control | — | 0.5919 ± 0.0518 |  |

*P < 0.05,
**P < 0.01 vs control.

The results showed that fusion protein I, protein II, protein III, protein IV, and protein V could inhibit mouse spleen lymphocytes to some extent compared with the ConA group.

Example 5

Effect of Fusion Protein I, Protein II, Protein III, Protein IV and Protein V on IL-1β Production by Mouse Peritoneal Macrophages (1) IL-1β production: mice were intraperitoneally injected with 1 mL of broth medium containing 6% starch, and three days later, the mouse peritoneal macrophages were aseptically taken, washed twice with a 1640 medium, and the cell concentration was adjusted to 2×10$^6$ cells/mL, inoculated into a 24-well culture plate at 1 mL/well, incubated for 3 h in a cell incubator, and shaken once every 30 min, so that the cells were allowed to adhere sufficiently. Then, the cells were washed twice with a culture liquid to remove un-adhered cells. The blank group was added with PBS, the positive group was added with the positive drug dexamethasone Dex, and the control group was the low, medium and high concentrations of fusion protein I, protein II, protein III, protein IV, protein V. After administration, the culture was continued for 48 h, the cells were centrifuged at 1000 r/min for 15 min. The supernatant was taken as a sample for testing activity of IL-1β.

(2) Determination of IL-1β content: the detection was performed by using mouse IL-1β enzyme-linked immunosorbent assay kit from R&D company. According to the instructions of the kit, the procedures were as follows: the reaction well for the test samples and different concentrations of standards were sealed with sealing tapes, respectively, incubation was performed at 37° C. for 90 min; the plate was washed four times; a biotinylated antibody working solution (100 μL/well) was added, the reaction well was sealed with sealing tapes, and incubation was performed at 37° C. for 60 min; the plate was washed four times; an enzyme conjugate working solution (100 μL/well) was added, the reaction well was sealed with sealing tapes, incubation was performed at 37° C. for 30 min; the plate was washed four times; a developer (100 μL/well) was added, incubation was performed at 37° C. for 10 to 20 min, a stop solution (100 μL/well) was added and mixed and the OD450 value was measured. The experimental results are shown in Table 11.

TABLE 11

Effect of fusion protein I, protein II, protein III, protein IV and protein V on IL-1β production by mouse peritoneal macrophages

| Group (n = 5) | Dose (μg/mL) | IL-1β (pg/mL) | PI (%) |
|---|---|---|---|
| Protein I | 8 | 731.65 ± 9.76 | 13.59% |
| | 32 | 470.01 ± 14.36* | 44.49% |
| | 128 | 318.44 ± 11.33** | 62.39% |
| Protein II | 8 | 746.38 ± 16.59 | 11.85% |
| | 32 | 596.02 ± 19.97* | 29.61% |
| | 128 | 440.56 ± 11.38** | 47.97% |
| Protein III | 8 | 741.77 ± 8.11 | 12.40% |
| | 32 | 496.11 ± 15.12* | 41.41% |
| | 128 | 302.13 ± 10.12** | 64.32% |
| Protein IV | 8 | 756.17 ± 9.21 | 10.70% |
| | 32 | 487.34 ± 14.11* | 42.44% |
| | 128 | 310.12 ± 11.18** | 63.37% |
| Protein V | 8 | 780.54 ± 10.23 | 7.82% |
| | 32 | 496.54 ± 12.65* | 41.36% |
| | 128 | 320.23 ± 13.76** | 62.18% |
| Dex | 20 | 310.25 ± 20.32** | 63.36% |
| Model group | | 846.73 ± 9.04** | 0.00% |
| control | — | 8.45 ± 2.23* | |

*$P < 0.05$,
**$P < 0.01$ vs control.

The results showed that fusion protein I, protein II, protein III, protein IV and protein V could significantly inhibit IL-1β production by mouse peritoneal macrophages.

Example 6

Effect of Fusion Protein I, Protein II, Protein III, Protein IV and Protein V on Subacute Inflammation of Tampon Granuloma in Rat 40 parts of degreasing cotton, 30 mg for each part, were accurately weighed with an analytical balance and kneaded into balls having substantially the same shape and size, which were autoclaved at 1.5 kpa for 30 min and dried at 50° C. for further use.

40 male SD rats were randomly divided into 4 groups with 10 rats for each group. The groups were a model group, a dexamethasone positive group (10 mg/kg), and fusion protein I, protein II, protein III, protein IV, protein V experimental groups at an effective dose of 64 mg/kg, respectively. Rats were anesthetized with sodium pentobarbital (40 mg/kg) via intraperitoneal injection before administration. The abdominal coat was cut off, and the skin of middle of the lower abdomen was cut under sterile conditions. The incision was about 1 cm long and the subcutaneous tissue was expanded with a vascular clamp. A sterile dry tampon was subcutaneously implanted into one side of the groin, the incision was sutured, and an appropriate amount of amoxicillin was spread at the incision to prevent infection. After the surgery was finished, the groups were administered once by injection from the day of surgery (EDSM needed to be administered twice a day). The rats were sacrificed by cervical dislocation at the 24th hour after administration, the inguinal skin was cut, the tampon was taken out together with the surrounding granulation tissue and the surrounding tissue was removed. After drying for additional 48 h in an oven at 60° C., the weight was accurately weighed. The granuloma weight was calculated: granuloma weight (mg/100 g body weight)=net weight of granulation (mg)/rat body weight (100 g). The experimental results are shown in Table 12.

TABLE 12

Effect of fusion protein I, protein II, protein III, protein IV, protein V on subacute inflammation of tampon granuloma in rat

| Group (n = 10) | Weight gain (g) | GranuLoma (mg)/Weight (100 g) | PI (%) |
|---|---|---|---|
| Protein I | 30.20 ± 11.84* | 0.25 ± 0.08* | 51.92% |
| Protein II | 32.16 ± 10.13* | 0.23 ± 0.05* | 55.77% |
| Protein III | 33.31 ± 8.17** | 0.34 ± 0.07** | 34.62% |
| Protein IV | 33.74 ± 12.12** | 0.45 ± 0.06** | 13.46% |
| Protein V | 32.45 ± 8.57** | 0.43 ± 0.05** | 17.31% |
| Dex(10 mg/kg) | −30.46 ± 6.28** | 0.21 ± 0.02** | 58.00% |
| control | 21.56 ± 7.28* | 0.52 ± 0.23* | |

*$P < 0.05$,
**$P < 0.01$ vs control.

The experimental results showed that fusion protein I, protein II, protein III, protein IV and protein V could significantly inhibit tampon granuloma in rat at an effective dose of 64 mg/kg, compared with the blank model group. Although the positive drug had a higher inhibition rate, the weight loss of the rat was obvious, and the side effects were larger. In contrast, the fusion protein was relatively safe.

Example 7

Effect of Fusion Protein I, Protein II, Protein III, Protein IV and Protein V on Peritoneal Capillary Permeability in Mice 80 Kunming mice were randomly divided into 8 groups with 10 mice for each group, which were a blank model group, a dexamethasone positive group (10 mg/kg), and fusion protein I, protein II, protein III, protein. IV, protein V experimental groups at high, medium and low doses (128, 32, 8 mg/kg), respectively. The drug was administered once by injection (EDSM needed to be administered twice a day), and the blank model group was given an equal volume of physiological saline and fed normally. On the 5th day, a 5 g/L Evans blue physiological saline solution was injected into the tail vein at 10 kg/mL, followed by intraperitoneal injection (10 kg/mL) of a HAc solution (6 mL/L) to induce inflammation. After 20 min, the mice were sacrificed by cervical dislocation. 5 mL of physiological saline was intraperitoneally injected, the abdomen was gently rubbed for 2 min, the abdominal cavity was cut, a peritoneal washing solution was collected and centrifuged at 4000 rpm for 10 min, 1 mL of supernatant was taken, and 3 mL of physiological saline was added to obtain 4 mL of dilution. The absorbance OD value of the dilution was measured by an ultraviolet spectrophotometer at a wavelength of 590 nm, and the amount of pigment exudation was expressed by the OD590 nm value, and the peritoneal capillary permeability in mice was examined. The experimental results are shown in Table 13.

TABLE 13

Effect of fusion protein I, protein II, protein III, protein IV, protein V on peritoneal capillary permeability in mice

| Group (n = 10) | Dose (mg/kg) | Exudation rate (OD590) | PI (%) |
|---|---|---|---|
| Protein I | 8 | 0.51 ± 0.04 | 26.09% |
| | 32 | 0.47 ± 0.03* | 31.88% |
| | 128 | 0.28 ± 0.06** | 59.42% |
| Protein II | 8 | 0.51 ± 0.06 | 26.09% |
| | 32 | 0.34 ± 0.03* | 50.72% |
| | 128 | 0.32 ± 0.07** | 53.62% |
| Protein III | 8 | 0.54 ± 0.04 | 21.74% |
| | 32 | 0.41 ± 0.07* | 40.58% |
| | 128 | 0.31 ± 0.03** | 55.07% |
| Protein IV | 8 | 0.56 ± 0.02 | 18.84% |
| | 32 | 0.36 ± 0.05* | 47.83% |
| | 128 | 0.28 ± 002** | 59.42% |
| Protein V | 8 | 0.55 ± 0.07 | 20.29% |
| | 32 | 0.39 ± 0.02* | 43.48% |
| | 128 | 0.26 ± 0.08** | 62.32% |
| Dex | 10 | 0.22 ± 0.03** | 68.12% |
| control | — | 0.69 ± 0.08* | |

*P < 0.05,
**P < 0.01 vs control.

The experimental results showed that fusion protein I, protein II, protein III, protein IV and protein V could significantly inhibit the increase of peritoneal capillary permeability in mice induced by glacial acetic acid. The higher the dose, the stronger the effect.

Example 8

Effect of Fusion Protein I, Protein II, Protein III, Protein IV, Protein V on Xylene-Induced Ear Swelling in Mice 80 Kunming mice were divided into 8 groups with 10 mice for each group and numbered. A physiological saline group was used as a blank control group, an aspirin group (200 mg/kg) was used as a positive control group, and fusion protein I, protein II, protein III, protein IV and protein V at high, medium and low doses (128, 32, 8 mg/kg) were used as experimental groups. Mice were administered once by injection, while EDSM needed to be administered twice a day for 5 consecutive days. The blank control group was given an equal volume of physiological saline. After the fifth day, 0.05 mL of xylene was applied to both sides of the right ears of the mice to induce inflammation, and the left ears were not applied and were normal ears. After 2 h, the mice were sacrificed by dislocation, and the ears were cut along the auricle. Ear pieces were taken with a puncher and weighed, and the swelling degree and swelling rate were calculated. Swelling degree=right ear piece weight-left ear piece weight, swelling rate=(swelling degree/left ear piece weight)×100%. The experimental results are shown in Table 14.

TABLE 14

Effect of fusion protein I, protein II, protein III, protein IV, protein V on xylene-induced ear swelling in mice

| Group (n = 10) | Dose (mg/kg) | Swelling degree (mg) | PI (%) |
|---|---|---|---|
| Protein I | 8 | 6.24 ± 0.26 | 6.17% |
| | 32 | 5.08 ± 0.32* | 23.61% |
| | 128 | 4.03 ± 0.27** | 39.40% |
| Protein II | 8 | 6.21 ± 0.23 | 6.62% |
| | 32 | 5.18 ± 0.89* | 22.11% |
| | 128 | 3.87 ± 0.45** | 41.80% |
| Protein III | 8 | 6.18 ± 0.29 | 7.07% |
| | 32 | 5.23 ± 0.16* | 21.35% |
| | 128 | 4.31 ± 0.22** | 35.19% |
| Protein IV | 8 | 6.32 ± 0.11 | 4.96% |
| | 32 | 5.47 ± 0.31* | 17.74% |
| | 128 | 4.22 ± 0.55** | 36.54% |
| Protein V | 8 | 6.14 ± 0.12 | 7.67% |
| | 32 | 5.34 ± 0.34* | 19.70% |
| | 128 | 4.76 ± 0.43** | 28.42% |
| Aspirin | 200 | 3.12 ± 0.34** | 53.08% |
| control | — | 6.65 ± 0.70* | |

*P < 0.05,
**P < 0.01 vs control.

The experimental results showed that high doses of fusion protein I, protein II, protein III, protein IV and protein V could significantly inhibit xylene-induced ear swelling in mice, and the inhibitory effect could be enhanced with the increase of dose.

Example 9

Effect of Fusion Protein I, Protein II, Protein III, Protein IV and Protein V on Acute Inflammation of Toe Swelling in Rat Induced by Carrageenan 80 SD rats were randomly divided into 8 groups with 10 mice for each group. The groups were a blank model group, a dexamethasone positive group (5 mg/kg) and fusion protein I, protein II, protein III, protein IV, protein V experimental groups at high, medium and low doses (128, 32, 8 mg/kg), respectively. The drug was administered once by injection, and the model group was given an equal volume of physiological saline and fed normally. On the third day, 0.1 mL of 1% carrageenan was injected subcutaneously into the right hind toes of the rats to induce inflammation. The foot volume was measured at 1 h, 3 h, 5 h, and 7 h after inflammation. The swelling degree of the foot was calculated according to the following formula: the swelling degree of the foot (mL)=the volume of the foot after inflammation—the volume before inflammation. The number of milliliters of spilled liquid was recorded (method: the protruding point of the right joint was circled with a ball-point pen and used as a measurement mark, and the right hind feet of the rat were sequentially placed in the volume measuring device, so that the hind limbs were exposed outside the cylinder, and the depth of the immersion was limited to the overlap of the circle and the liquid level. After the foot entered the liquid, the liquid level was raised, and the volume of the spilled liquid was the volume of the right hind foot of the rat, and the normal volume of the right hind foot of each rat is sequentially determined). The experimental results are shown in Table 15.

TABLE 15

Effect of fusion protein I, protein II, protein III, protein IV, protein V on acute inflammation of toe swelling in rat induced by carrageenan

| Group (n = 10) | Dose (mg/kg) | Swelling degree (mL) | | | |
|---|---|---|---|---|---|
| | | 1 h | 3 h | 5 h | 7 h |
| Protein I | 8 | 0.26 ± 0.15 | 0.33 ± 0.12 | 0.42 ± 0.14 | 0.36 ± 0.11* |
| | 32 | 0.22 ± 0.19* | 0.35 ± 0.17 | 0.31 ± 0.15* | 0.37 ± 0.18* |
| | 128 | 0.27 ± 0.12* | 0.38 ± 0.16** | 0.34 ± 0.14* | 0.43 ± 0.16** |
| Protein II | 8 | 0.29 ± 0.25** | 0.34 ± 0.09* | 0.36 ± 0.12 | 0.41 ± 0.09* |
| | 32 | 0.27 ± 0.06 | 0.41 ± 0.18* | 0.37 ± 0.11* | 0.33 ± 0.02** |
| | 128 | 0.21 ± 0.16* | 0.32 ± 0.10* | 0.41 ± 0.05 | 0.36 ± 0.16** |
| Protein III | 8 | 0.24 ± 0.04 | 0.37 ± 0.16* | 0.35 ± 0.07 | 0.41 ± 0.18* |
| | 32 | 0.28 ± 0.17* | 0.31 ± 0.22** | 0.37 ± 0.14* | 0.39 ± 0.12** |
| | 128 | 0.24 ± 0.12* | 0.36 ± 0.11** | 0.40 ± 0.10* | 0.43 ± 0.18** |
| Protein IV | 8 | 0.23 ± 0.09* | 0.34 ± 0.12 | 0.46 ± 0.07* | 0.33 ± 0.14** |
| | 32 | 0.29 ± 0.16 | 0.35 ± 0.10* | 0.48 ± 0.09 | 0.32 ± 0.13** |
| | 128 | 0.27 ± 0.13 | 0.42 ± 0.15* | 0.34 ± 0.19 | 0.45 ± 0.16** |
| Protein V | 8 | 0.25 ± 0.10** | 0.30 ± 0.08 | 0.41 ± 0.06 | 0.40 ± 0.08* |
| | 32 | 0.23 ± 0.16** | 0.39 ± 0.09 | 0.38 ± 0.05* | 0.46 ± 0.17** |
| | 128 | 0.22 ± 0.09* | 0.33 ± 0.15 | 0.47 ± 0.04 | 0.35 ± 0.19** |
| Dex | 10 | 0.21 ± 0.11** | 0.23 ± 0.04 | 0.25 ± 0.09 | 0.27 ± 0.12* |
| control | — | 0.23 ± 0.12 | 0.43 ± 0.08 | 0.51 ± 0.05 | 0.31 ± 0.23 |

*$P < 0.05$,
**$P < 0.01$ vs control.

The experimental results showed that the toes of the rats in each group were rapidly swollen after modeling, and the peak of swelling was reached at about 3-5 h, which began to subside at 7 h. The fusion protein I, protein II, protein III, protein IV and protein V at high doses could significantly inhibit toe swelling in rat induced by carrageenan, and the inhibitory effect was not significant at low dose.

Example 10

Effect of Fusion Protein I, Protein II, Protein III, Protein IV and Protein V on Chronic Inflammation of Adjuvant Arthritis in Rat Model Establishment:

80 SPF SD rats were randomly divided into 8 groups. Rats in each group were lightly anesthetized with ether. Then, 0.1 mL of complete Freund's adjuvant containing inactivated *Mycobacterium tuberculosis* was injected subcutaneously into the left hind foot of the rats. Primary arthritis occurred in the left hind foot of the rat, and at about 13 days post-modeling, secondary arthritis occurred in the right hind foot. A blank control group was injected with an equal volume of physiological saline. The drug was administered 13 days after modeling. A methotrexate group was administered by injection every 5 days for 15 days, 4 times in total; the fusion protein I, protein II, protein III, protein IV, and protein V at high, medium and low doses (128 mg/kg, 32 mg/kg, 8 mg/kg) were administered by injection every 5 days for 15 days.

Efficacy Evaluation:

1. Primary and Secondary Toe Swelling Degree

Using a foot volume measuring method, a marker was made with a fat-soluble marker at the left and right posterior ankle joint of each rat, and the left and right hind feet of the animal were respectively immersed in the volume measuring device. The immersion depth was bounded by the marker, and the reading value at the scale pipette of the device was the initial volume of the animal's left and right hind feet.

The day of modeling was considered as the 0th day and recorded as d0. The volume of the left hind foot (modeling foot) was measured from the first day d1 after modeling every 2 days. When the swelling occurred (i.e., secondary arthritis occurred) at the contralateral non-inflammatory foot (right hind foot), the administration was started. The volume of the left and right hind feet was measured every 2 days, and the degree of primary and secondary toe swelling was determined, which was calculated as follows:

Primary toe swelling (mL)=left hind foot volume on the day of measurement-initial volume of left hind foot Secondary toe swelling (mL)=right hind foot volume on the day of measurement-initial volume of right hind foot 2. Clinical score Systemic score: the systemic score was taken every 2 days after the onset of secondary inflammation.

Hind foot: no swelling=0 score, one hind foot swelling=1 score, two hind feet swelling=2 scores;

Forefoot: no swelling=0 score, one forefoot swelling=1 score, two forefeet swelling=2 scores;

Ear: no redness and nodules=0 score, redness or nodules in one ear=1 score, redness and nodules in both ears=2 scores;

Nose: no swelling=0 score, obvious swelling=1 score;

Tail: no nodules=0 score, with nodules=1 score; full score was 8 scores.

Arthritis index score: the arthritis index score was performed every 2 days after the onset of secondary inflammation.

Normal=0 score; erythema and mild swelling in the ankle joint=1 score; erythema and mild swelling from the ankle to the metatarsophalangeal joint or metacarpal joint=2 scores; erythema and moderate swelling from the ankle to the metatarsophalangeal joint or metacarpal joint=3 scores; erythema and severe swelling from the ankle to the metatarsophalangeal joint or metacarpal joint=4 scores; each foot had a full score of 4 scores, and each rat had a maximum score of 16 scores.

3. Weight Gain

The initial body weight of each group of rats was weighed before modeling. The body weight was measured every 2 days from d1 after modeling, from which the initial body weight was subtracted to obtain the weight gain of each group of rats. The experimental results are shown in Table 16.

TABLE 16

Effect of fusion protein I, protein II, protein III, protein IV, protein V on chronic inflammation of adjuvant arthritis in rat

| Group (n = 10) | Dose (mg/kg) | Foot swelling degree (mL) | | | Clinical score | |
|---|---|---|---|---|---|---|
| | | Left | Right | Whole body | Arthritis index | Weight gain (g) |
| Protein I | 8 | 1.76 ± 0.31 | 1.92 ± 0.09 | 2.11 ± 0.16* | 6.77 ± 0.53 | 43.97 ± 20.59 |
| | 32 | 1.62 ± 0.11** | 1.54 ± 0.17* | 1.82 ± 0.35 | 5.71 ± 0.38* | 49.02 ± 17.15* |
| | 128 | 1.41 ± 0.22** | 1.34 ± 0.08** | 1.55 ± 0.10** | 4.44 ± 0.48** | 52.15 ± 15.91* |
| Protein II | 8 | 1.95 ± 0.12 | 1.77 ± 0.54 | 2.23 ± 0.26* | 6.92 ± 0.55 | 44.96 ± 12.11 |
| | 32 | 1.60 ± 0.19* | 1.54 ± 0.33* | 1.81 ± 0.32 | 5.69 ± 0.37* | 48.10 ± 9.19* |
| | 128 | 1.35 ± 0.14** | 1.35 ± 0.73* | 1.54 ± 0.19** | 4.17 ± 0.64** | 50.83 ± 15.19** |
| Protein III | 8 | 1.91 ± 0.29 | 1.94 ± 0.16 | 1.87 ± 0.22 | 6.78 ± 0.54 | 44.27 ± 15.33 |
| | 32 | 1.63 ± 0.08** | 1.61 ± 0.21* | 1.77 ± 0.37 | 5.64 ± 0.46* | 48.02 ± 14.66* |
| | 128 | 1.34 ± 0.23** | 1.41 ± 0.08** | 1.52 ± 0.07** | 4.44 ± 0.49** | 51.55 ± 12.10** |
| Protein IV | 8 | 1.89 ± 0.31 | 1.91 ± 0.09 | 2.09 ± 0.17* | 6.79 ± 0.52 | 43.82 ± 19.04 |
| | 32 | 1.66 ± 0.08** | 1.57 ± 0.20* | 1.84 ± 0.39 | 5.73 ± 0.47* | 47.09 ± 17.75* |
| | 128 | 1.39 ± 0.21** | 1.36 ± 0.06** | 1.54 ± 0.07** | 4.41 ± 0.45** | 53.63 ± 12.29* |
| Protein V | 8 | 1.92 ± 0.09 | 1.76 ± 0.55 | 2.21 ± 0.24* | 6.95 ± 0.56 | 44.75 ± 17.46 |
| | 32 | 1.61 ± 0.21* | 1.59 ± 0.31* | 1.86 ± 0.34 | 5.71 ± 0.42* | 47.33 ± 15.29* |
| | 128 | 1.32 ± 0.16** | 1.33 ± 0.72* | 1.53 ± 0.18** | 4.19 ± 0.65** | 51.97 ± 9.03** |
| Methotrexate | 1 | 1.19 ± 0.20** | 1.22 ± 0.13** | 1.31 ± 0.17** | 2.00 ± 0.54** | 47.32 ± 17.20** |
| control | — | 2.14 ± 0.07 | 2.06 ± 0.16 | 2.61 ± 0.26 | 7.52 ± 0.35 | 29.51 ± 19.94 |

*P <0.05,
**P <0.01 vs control.

The experimental results showed that after modeling, the left hind foot in each group was swollen rapidly (primary inflammation), and on the 13th day, the hind foot (non-contralateral inflammatory foot) began to be red and swollen (i.e., secondary inflammation occurred). The arthritis index and systemic score began to increase, reaching the highest value on the 19th day, and the swelling degree and score of each group are gradually decreased along with administration. The primary toe swelling degree was used to reflect the therapeutic effect of each treatment group on primary arthritis. The high and medium doses of each administration group could treat primary arthritis to a certain extent compared with the model group. The positive drug methotrexate had the best effect, and the fusion protein I, protein II, protein III, protein IV, and protein V were effective in high dose groups, with extremely significant differences (**P<0.01). The secondary toe swelling degree was used to reflect the therapeutic effect of each treatment group on secondary arthritis.

Example 11

Inhibitory Effect of Fusion Protein I, Protein II, Protein III, Protein IV and Protein V on Proliferation of Human Retinal Vascular Endothelial Cell (HRCEC)

The activity of the integrin blocker polypeptide to inhibit proliferation of human retinal vascular endothelial cells was examined by MTT assay. HRCEC cells were cultured in a 5% $CO_2$ incubator at 37° C. to a density of 90% or more, and then collected by trypsinization. The cells were resuspended in the culture liquid and counted under a microscope. The cell concentration was adjusted to $3.0 \times 10^4$ cells/mL. The cell suspension was inoculated into a 96-well plate at 100 μL per well and cultured in a 5% $CO_2$ incubator at 37° C. overnight. The polypeptide I, the polypeptide II, the polypeptide III, and the Avastin were diluted with the culture liquid to respective predetermined concentrations. After the cells were fully adhered, each dilution was added to a 96-well plate at 100 μL per well, respectively. The integrin blocker polypeptide was used as a administration group, and Avastin was used as a positive control group, and a culture liquid containing no drug was used as a blank control group, which were incubated in a 5% $CO_2$ incubator at 37° C. for 48 hours. 20 μL of 5 mg/mL MTT was added to each well of a 96-well plate, and incubation was continued for 4 hours. The medium was aspirated and 100 μL of DMSO was added per well for dissolution. The absorbance was measured at 570 nm with a microplate reader with a reference wavelength of 630 nm, and the proliferation inhibition (PI) was calculated. The formula was as follows:

$$PI(\%) = 1 - \frac{N_{test}}{N_{control}} \times 100\%$$

where $N_{test}$ is the OD value of the test group and $N_{control}$ is the OD value of the blank control group.

Data Statistics:

The test was repeated 5 times independently. The results obtained from the test were calculated as mean±SD, and statistical t-test was performed. P<0.05 was considered as significant difference, and P<0.01 was considered as extremely significant difference. The experimental results are shown in Table 17.

TABLE 17

Inhibitory effect of fusion protein I, protein II, protein III, protein IV, and protein V on proliferation of human retinal vascular endothelial cell (HRCEC)

| Group (n = 5) | Dose (μg/mL) | A570 nm/A630 nm | PI (%) |
|---|---|---|---|
| Protein I | 1 | 1.1856 ± 0.0395 | 11.99% |
| | 2 | 1.0024 ± 0.0401 | 25.59% |
| | 4 | 0.9248 ± 0.0383 | 31.35% |
| | 8 | 0.9014 ± 0.0368 | 33.09% |
| | 16 | 0.8314 ± 0.0344 | 38.28% |
| | 32 | 0.7284 ± 0.0299 | 45.93% |
| | 64 | 0.5879 ± 0.0327 | 56.36% |
| | 128 | 0.3849 ± 0.0311 | 71.43% |
| | 256 | 0.1488 ± 0.0296 | 88.95% |
| Protein II | 1 | 1.1122 ± 0.0385 | 17.44% |
| | 2 | 1.0002 ± 0.0405 | 25.75% |
| | 4 | 0.9287 ± 0.0288 | 31.06% |
| | 8 | 0.8999 ± 0.0320 | 33.20% |
| | 16 | 0.8225 ± 0.0291 | 38.94% |

TABLE 17-continued

Inhibitory effect of fusion protein I, protein II, protein III, protein IV, and protein V on proliferation of human retinal vascular endothelial cell (HRCEC)

| Group (n = 5) | Dose (μg/mL) | A570 nm/A630 nm | PI (%) |
|---|---|---|---|
| | 32 | 0.7348 ± 0.0277 | 45.45% |
| | 64 | 0.5748 ± 0.0314 | 57.33% |
| | 128 | 0.3628 ± 0.0282 | 73.07% |
| | 256 | 0.1495 ± 0.0314 | 88.90% |
| Protein III | 1 | 1.1125 ± 0.0403 | 17.42% |
| | 2 | 0.9945 ± 0.0375 | 26.17% |
| | 4 | 0.9168 ± 0.0362 | 31.94% |
| | 8 | 0.8997 ± 0.0358 | 33.21% |
| | 16 | 0.8347 ± 0.0274 | 38.04% |
| | 32 | 0.7451 ± 0.0280 | 44.69% |
| | 64 | 0.5974 ± 0.0193 | 55.65% |
| | 128 | 0.3789 ± 0.0238 | 71.87% |
| | 256 | 0.1453 ± 0.0247 | 89.21% |
| Protein IV | 1 | 1.1002 ± 0.0393 | 18.33% |
| | 2 | 0.9999 ± 0.0385 | 25.77% |
| | 4 | 0.9146 ± 0.0374 | 32.11% |
| | 8 | 0.8858 ± 0.0389 | 34.24% |
| | 16 | 0.8367 ± 0.0351 | 37.89% |
| | 32 | 0.7386 ± 0.0294 | 45.17% |
| | 64 | 0.5613 ± 0.0273 | 58.33% |
| | 128 | 0.3741 ± 0.0284 | 72.23% |
| | 256 | 0.1552 ± 0.0277 | 88.48% |
| Protein V | 1 | 1.0522 ± 0.0379 | 21.89% |
| | 2 | 0.9858 ± 0.0335 | 26.82% |
| | 4 | 0.9154 ± 0.0342 | 32.05% |
| | 8 | 0.8991 ± 0.0328 | 33.26% |
| | 16 | 0.8298 ± 0.0294 | 38.40% |
| | 32 | 0.7288 ± 0.0276 | 45.90% |
| | 64 | 0.5589 ± 0.0243 | 58.51% |
| | 128 | 0.3652 ± 0.0222 | 72.89% |
| | 256 | 0.1467 ± 0.0199 | 89.11% |
| Taxol | 5 | 0.2387 ± 0.0257 | 82.28% |
| control | — | 1.3471 ± 0.0583 | 0.00% |

*$P < 0.05$,
**$P < 0.01$ vs control.

The results showed that fusion protein I, protein II, protein III, protein IV and protein V could significantly inhibit the proliferation of human retinal vascular endothelial cells (HRCEC) in a dose-dependent manner. At a concentration of 64 μg/mL, the inhibition rate reached 50% or more.

Example 12

Activity of Fusion Protein I, Protein II, Protein III, Protein IV, Protein V to Inhibit Angiogenesis In Vivo Analyzed by Chicken Embryo Chorioallantoic Membrane (CAM)

In this study, CAM assay was used to investigate the activity of fusion protein I, protein II, protein III, protein IV, and protein V to inhibit angiogenesis in vivo. The study has shown that the biosynthesis rate of collagen reached the maximum on the 8th to 11th day of chicken embryo development, which was the most vigorous stage of angiogenesis, and the body's immune system had not yet been fully established at that time, and thus the chicken embryos developed to the 8th day was selected to be administered. Considering that the polypeptide on drug-loaded paper had a certain diffusion range limitation on the chicken embryo chorioallantoic membrane, only the number of new blood vessels within a radius of 5 mm from the edge of the paper was counted in the test. The following steps were used.

(1) The White Leghorn chicken embryos on day 6 were cultured in a 37° C. incubator at 60%-70% humidity for two days.

(2) A 1.0 cm×1.0 cm window was drilled above the chicken embryo air sac, and the inner membrane was torn off with forceps to expose the chorioallantoic membrane. Lens paper having a diameter of 5 mm was used as a loading carrier, and was placed on the chorioallantoic membrane of the chicken embryo air sac. Filter paper with PBS was used as a blank group, and the administration group was added with different doses of fusion protein. The positive control was Avastin.

(3) The chicken embryo air sac was sealed with a sterile transparent tape, and after culturing at 37° C. for 72 hours, the chicken embryo air sac was opened, and a fixative (formaldehyde:acetone=1:1) was added for fixation for 15 minutes. The chorioallantoic membrane to which the lens paper was adhered was taken out, the distribution of the new blood vessels was observed, and the new blood vessels were counted and photographed. Five replicates were set for each dose and the results were statistically analyzed.

The analysis results of the activity of fusion protein to inhibit angiogenesis in vivo by the chicken embryo chorioallantoic membrane (CAM) assay were as follows: negative control was treated with PBS, the dose of positive control Avastin was 10 fusion protein I, protein II, protein III, protein IV, protein V were used to treat the chicken embryos at high, medium and low doses of 128 μg, 32 μg and 8 μg, respectively. The results are shown in Table 18.

TABLE 18

Inhibitory effect of fusion protein I, protein II, protein III, protein IV, protein V on angiogenesis of chicken embryo chorioallantoic membrane

| Group (n = 5) | Dose (μg) | Blood vessel number | PI (%) |
|---|---|---|---|
| Protein I | 8 | 93 ± 5 | 24.39% |
| | 32 | 76 ± 2 | 38.21% |
| | 128 | 50 ± 9** | 59.35% |
| Protein II | 8 | 102 ± 10 | 17.07% |
| | 32 | 83 ± 11 | 32.52% |
| | 128 | 66 ± 7* | 46.34% |
| Protein III | 8 | 93 ± 7 | 24.39% |
| | 32 | 75 ± 1 | 39.02% |
| | 128 | 49 ± 10** | 60.16% |
| Protein IV | 8 | 101 ± 9 | 17.89% |
| | 32 | 81 ± 11 | 34.15% |
| | 128 | 64 ± 9* | 47.97% |
| Protein V | 8 | 98 ± 8 | 20.33% |
| | 32 | 84 ± 10 | 31.71% |
| | 128 | 65 ± 8* | 47.15% |
| Avastin | 10 | 57 ± 16** | 53.66% |
| control | — | 123 ± 13 | 0.00% |

*$P < 0.05$,
**$P < 0.01$ vs control.

The results showed that fusion protein I, protein II, protein III, protein IV, and protein V could inhibit angiogenesis of CAM, and had a strong inhibitory effect (nearly 50%) at high dose.

Example 13

Effect of Fusion Protein I, Protein II, Protein III, Protein IV and Protein V on Corneal Neovascularization in Mice (1) Preparation of Corneal Neovascularization Model Induced by Alkali Burn in BALB/c Mice:

15 healthy male BALB/c mice with weight of 20-25 g were examined under a slit lamp microscope for the anterior segment of both eyes and the appendage to exclude ocular lesions. The eyes were given 0.3% loxacin eye drops 1 day before the preparation of alkali burn model, twice a day. After the mice were anesthetized by intraperitoneal injection of 1.8% Avertin, single-layer filter paper with a diameter of 2 mm was clamped with tweezers, and immersed in a 1 mol/L sodium hydroxide solution to reach a saturated state, and the excess liquid was removed. The filter paper was placed in the central corneal of BALB/c mice for 40 s and then discarded, and the burned area and conjunctival sac were immediately rinsed with 15 mL of PBS for 1 min. Excess water was wiped away with cotton swabs, and under an operating microscope, the corneal epithelium was vortically scraped off by paralleling a corneal scraping knife to the limbus corneae. The subcutaneous stromal layer and limbus corneae was carefully not to be injured, and after surgery, an erythromycin eye ointment was applied into the conjunctival sac to prevent infection.

(2) Experimental Animal Grouping and Sample Acquisition:

15 mice were randomly divided into fusion protein I, protein II, protein III, protein IV, protein V groups and a control group, with 5 rats in each group. After alkali burn, 64 μg of fusion protein I, protein II, protein III, protein IV, protein V and physiological saline were given via intravitreal injection once every 3 days for 1 week, and the inflammatory reaction and neovascularization of the cornea in each group were observed under a slit lamp microscope on day 1, day 7, and day 14 after alkali burn. On day 14 after alkali burn, the neovascularization of the corneal in each group was photographed and recorded under the slit lamp microscope for photographing anterior segment of the eye. Then, all the mice were sacrificed by cervical dislocation and the eyeballs were removed. The blood was washed with physiological saline, and the eyeballs were fixed in 4% paraformaldehyde for 1.5 h, dehydrated in PBS containing 30% sucrose overnight, embedded in an OCT tissue freezing medium, stored in a refrigerator at −80° C., subjected to cryosection at 8 and detected by immunohistochemistry for CD31 expression.

(3) Quantitative Measurement for Microvessel Density of Corneal Tissue:

Microvessel density (MVD) is an indicator for evaluating angiogenesis. An anti-CD31 antibody immunohistochemistry was used to label vascular endothelial cells and the number of microvessels per unit area was counted to measure the extent of neovascularization. Standards for counting microvessels were that under a microscope, the endothelial cells or cell clusters which were clearly demarcated from adjacent tissues in the corneal tissue and were stained tan or brown were counted as the new blood vessels. The number of new blood vessels in the entire section was counted under a 10×20 microscope. After the corneal tissue was photographed, the area of the entire corneal tissue was calculated by image processing software Image J, and the density of new blood vessels in the entire section in this example was determined. The results are shown in Table 19.

TABLE 19

MVD count showing effect of fusion protein I, protein II, protein III, protein IV, protein V on corneal neovascularization in mice

| Group (n = 5) | Dose (μg) | MVD |
|---|---|---|
| Protein I | 64 | 26.94 ± 5.91* |
| Protein II | 64 | 24.64 ± 4.24* |
| Protein III | 64 | 25.74 ± 5.39* |
| Protein IV | 64 | 24.62 ± 4.81* |
| Protein V | 64 | 25.57 ± 4.76* |
| control | — | 51.03 ± 7.57* |

*$P < 0.05$,
**$P < 0.01$ vs control.

The results showed that CD31 was used as a microvascular marker, which was mainly expressed in the cytoplasm of vascular endothelial cells. The stained positive cells were vascular endothelial cells stained tan or brown without background staining. The number of CD31-positive new blood vessels in fusion protein I, protein II, protein III, protein IV, protein V experimental groups was significantly reduced compared with that of the control group. Fusion protein I, protein II, protein III, protein IV, and protein V groups had significant difference compared with the control group. The experimental results showed that fusion protein I, protein II, protein III, protein IV, protein V could inhibit the growth of corneal new blood vessels, and can be used as a medicament for the treatment of corneal neovascular eye diseases.

Example 14

Effect of Fusion Protein I, Protein II, Protein III, Protein IV and Protein V on Iris Neovascularization in Rabbits The argon ion laser at 577 nm was used to occlude the major branch vein of rabbit retina, and a success venous occlusion was confirmed by fundus fluorescein angiography (FFA). After 5-12 days, the iris fluorescein angiography (IFA) showed that the fluorescein leakage was obvious in the iris vessels compared with the normal control group, confirming the formation of the animal model of the iris neovascularization (NVI).

9 eyes successful in modeling were randomly divided into 3 groups with 3 eyes for each group. They were labeled as a negative control group, and fusion protein I, protein II, protein III, protein IV and protein V treatment groups, respectively, which were respectively given physiological saline, 128 μg of fusion protein I, 128 μg of protein II, 128 μg of protein III, 128 μg of protein IV and 128 μg of protein V via intravitreal injection once every 5 days for 2 weeks. The observation was performed with an optical and electron microscope on the third week.

Results: under the optical microscope, it was observed that the anterior surface of the iris was a fibrous vascular membrane remnant mainly consisting of fibrous tissue, and there were few open vascular lumens. Vascular residues can be seen in the iris matrix, which are necrotic cells and cell debris. The iris surface of the control eye under a light microscope is a fibrous vascular membrane with branches and potential lumens.

The ultrastructure of the iris in the treatment group showed a series of degenerative changes. The endothelial cells of the large blood vessels in the middle of the iris matrix had normal nucleus, cytoplasm and cell junctions. There were capillary residues in the iris matrix and on the anterior surface of the iris, which were surrounded by cell debris and macrophage infiltration. No capillary with potential lumens and degenerated parietal cells indicated regression of new blood vessels.

Through animal model experiments of iris neovascularization, it was demonstrated that fusion protein I, protein II, protein III, protein IV, and protein V could inhibit neovascularization and regress the formed blood vessels.

Example 15

Effect of Fusion Protein I, Protein II, Protein III, Protein IV and Protein V on Choroidal Blood Flow in Rabbit Eyes New Zealand white rabbits with weight of 2.5-3.0 kg were randomly divided into 3 groups, which were labeled as a control group, and fusion protein I, protein II, protein III, protein IV, and protein V groups. White rabbits in each group were anesthetized with 35 mg/kg xylazine via intramuscular injection, and then anesthesia was maintained with half of the initial amount via intramuscular injection per hour. The intraocular pressure of the left eye was increased to 40 mmHg, under which the blood flow can be reduced to ⅓ of the normal value. The left ventricle was cannulated through right carotid artery for injection of microspheres (for the calculation of ocular blood flow), and the femoral artery was cannulated for blood collection. Each group was given physiological saline, 128 μg of fusion protein I, 128 μg of protein II, 128 μg of protein III, 128 μg of protein IV, and 128 μg of protein V via intravitreal injection. The ocular blood flow of rabbit eyes with high intraocular pressure was measured by a color microsphere technique at 0, 30, and 60 minutes after administration. At each time point, 0.2 mL (about 2 million) of microspheres were injected. Immediately after the microspheres were injected, blood was collected through the femoral artery for 60 seconds, and placed in a heparinized anticoagulant tube, and the amount of blood collected was recorded. After the last blood collection, the animals were sacrificed with 100 mg/kg phenobarbital via intravenous infusion. The eyeballs were removed, and the retina, choroid, iris and ciliary body were separated, and the tissue weight was recorded. The tissue blood flow at each time point was calculated with the following formula: $Qm = (Cm \times Qr)/Cr$, where $Qm$ represented tissue blood flow in μL/min/mg; $Cm$ was the number of microspheres per milligram of tissue; $Qr$ was blood flow in μL/min; and $Cr$ was the number of blood microspheres as a reference. The experimental results are shown in Table 20.

TABLE 20

Effect of fusion protein I, protein II, protein III, protein IV, protein V on choroidal blood flow in white rabbit eyes

| Group (n = 3) | Dose (μg) | Time (min) | Blood flow (μL/min/mg) |
|---|---|---|---|
| Protein I | 128 | 0 | 21.9 ± 2.3 |
| | 128 | 30 | 16.9 ± 3.1 |
| | 128 | 60 | 15.1 ± 1.6 |
| Protein II | 128 | 0 | 22.9 ± 2.5 |
| | 128 | 30 | 15.7 ± 1.3 |
| | 128 | 60 | 13.9 ± 1.2 |
| Protein III | 128 | 0 | 22.1 ± 2.2 |
| | 128 | 30 | 17.1 ± 2.9 |
| | 128 | 60 | 14.9 ± 1.5 |
| Protein IV | 128 | 0 | 22.7 ± 2.4 |
| | 128 | 30 | 15.5 ± 1.2 |
| | 128 | 60 | 13.7 ± 1.3 |
| Protein V | 128 | 0 | 22.8 ± 2.1 |
| | 128 | 30 | 15.8 ± 1.4 |
| | 128 | 60 | 13.8 ± 1.1 |
| control | — | 0 | 11.9 ± 1.2 |
| | — | 30 | 9.5 ± 1.4 |
| | — | 60 | 5.3 ± 1.7 |

The results showed that choroidal blood flow was significantly increased in the fusion protein I, protein II, protein III, protein IV, and protein V treatment groups at all observation time points.

Example 16

Effect of Fusion Protein I, Protein II, Protein III, Protein IV, and Protein V on Retinal Blood Vessels in OIR Mice Establishment of the OIR model: young mice and their mothers were exposed to 75% hyperoxic environment from day 7 to day 12 after birth of C57/B16 mice so that capillaries in the central retina rapidly disappeared. On day 12, the mice were returned to indoor air and the retinal blood vessels exposed to hyperoxia rapidly disappeared, which caused extensive abnormal neovascularization, and the central part of the retina remained largely avascular for a long time. After the blood vessels disappeared completely, the fusion protein (administration group, the doses of fusion protein I, protein II, protein III, protein IV, and protein V were all 64 μg) or physiological saline (negative group) was injected into the vitreous body on day 13. Retinal vessels were evaluated on day 17 (labeled as unclosed vessels, 50 mL of Texas Red-labeled tomato lectin was injected into the left ventricle and cycled for 5 minutes). The experimental results are shown in Table 21.

TABLE 21

Effect of fusion protein I, protein II, protein III, protein IV, protein V on retinal blood vessels in OIR mice

| Group (n = 5) | Dose (μg) | Area (mm$^2$) | Reduce (%) |
|---|---|---|---|
| Protein I | 64 | 0.101 ± 0.036* | 52.13% |
| Protein II | 64 | 0.146 ± 0.011* | 30.81% |
| Protein III | 64 | 0.104 ± 0.041* | 50.71% |
| Protein IV | 64 | 0.152 ± 0.013* | 27.96% |
| Protein V | 64 | 0.144 ± 0.015* | 31.75% |
| control | — | 0.211 ± 0.039 | 0.00% |

*$P < 0.05$,
**$P < 0.01$ vs control.

The results showed that the administration of fusion protein I, protein II, protein III, protein IV, and protein V to OIR mice could alleviate pathological neovascularization. Compared with the negative control, the neovascular clusters in the retina of OIR mice treated with fusion protein I, protein II, protein III, protein IV, and protein V were significantly reduced, and the areas occupied by neovascular clusters were decreased by 52.13%, 30.81%, 50.71%, 27.96%, and 31.75%, respectively.

Example 17

Effect of Fusion Protein I, Protein II, Protein III, Protein IV and Protein V on Neovascularization in Premature Rat Retinopathy Model A fluctuating oxygen-induced animal model was adopted, and newborn rats (within 12 hours) spontaneously delivered on the same day were randomly divided into three groups: an oxygen model group, an oxygen treatment group, and a normal control group. The oxygen model was subdivided into three model subgroups, which were placed in a semi-closed oxygen chamber made of plexiglass together with the treatment group. The medical oxygen was introduced into the chamber, and the oxygen concentration was adjusted to 80%±2% with an oxygen meter. After 24 hours, nitrogen gas was introduced into the oxygen chamber, and then the oxygen concentration was rapidly adjusted to 10%±2% and maintained for 24 hours. The operation was repeated, the oxygen concentration in the oxygen chamber was maintained to be alternated between 80% and 10% every 24 hours for 7 days, and then the rats were transferred to the air and fed. The oxygen concentration was monitored 8 times a day, and the ambient temperature in the chamber was controlled to 23° C.±2° C. The litter was replaced, food was added, water was changed, and mother rat was replaced once. The normal control group was placed in an animal house feeding environment. Compared with the control group, if the retinal stretched preparation stained with ADPase in the model group showed obvious vascular changes, the nucleus count of vascular endothelial cells that broke through the inner limiting membrane of the retina into the vitreous body was increased, and the difference was statistically significant, the model was successfully established.

The oxygen treatment group was divided into two sub-groups. On day 7 of modeling, the administration was performed via intravitreal injection, in which the fusion protein I, protein II, protein III, protein IV, and protein V were administered at a dose of 100 respectively. The oxygen model group and the control group were given only physiological saline for one week.

On day 14, after the rats was sacrificed with ether anesthesia, the eyeballs were removed and fixed in a 40 g/L paraformaldehyde solution for 24 hours. The eyeballs were dehydrated with gradient alcohols and hyalinized with xylene. After being immersed in wax, the eyeballs were continuously sectioned to a thickness of 4 avoiding the surrounding of the optic disc as much as possible. The sections were parallel to the sagittal plane of the cornea to the optic disc. 10 sections were randomly selected from each eyeball to be stained with hematoxylin and eosin, and the nucleus of vascular endothelial cells that broke through the inner limiting membrane of the retina was counted (only the nucleus of vascular endothelial cells closely related to the inner limiting membrane were counted), and the average number of cells per section per eyeball was counted.

Results: no or few nucleus of vascular endothelial cells that broke through the inner limiting membrane of the retina into the vitreous body was found in the control group. More nucleuses of vascular endothelial cell that broke through the inner limiting membrane of the retina were found in the model group, some of which appeared alone, some clustered, and some nucleuses of vascular endothelial cells were found to be adjacent to the deep retinal vessels on some sections, confirming that they were originated from the retina instead of the vitreous body or other tissues in eyes. Only a few nucleuses of vascular endothelial cell that broke through the inner limiting membrane of the retina were found in the sections of the treatment group. The experimental results are shown in Table 22.

TABLE 22

Nucleus count of vascular endothelial cells in each group

| Group | Dose (µg) | Nucleus number |
|---|---|---|
| Protein I | 100 | 6.502 ± 2.011 |
| Protein II | 100 | 7.238 ± 1.194 |
| Protein III | 100 | 6.471 ± 2.017 |
| Protein IV | 100 | 7.226 ± 1.215 |
| Protein V | 100 | 6.954 ± 1.003 |
| Model group | — | 26.945 ± 1.943 |
| control | — | 1.199 ± 0.297 |

The results showed that the nucleus counts of retinal vascular endothelial cells in the fusion protein I, protein II, protein III, protein IV, and protein V treatment groups were 6.502±2.011, 7.238±1.194, 6.471±2.017, 7.226±1.215, and 6.954±1.003, compared with the oxygen model group (27.452±2.110), the nucleus counts of retinal vascular endothelial cells were significantly reduced, which proved that they can inhibit the neovascularization in the oxygen-induced neonatal rat retinopathy model to a certain extent.

Example 19

Effect of Fusion Protein I, Protein II, Protein III, Protein IV and Protein V on Neovascularization in Diabetic Retinopathy Rat Model The experimental diabetic rat model was established with streptozotocin STZ. STZ was dissolved in 0.1 mol/L citrate buffer at pH 4.5 to prepare a 2% solution. All experimental Wistar rats were fasted for 12 h before injection, and each rat was intraperitoneally injected with a 2% STZ solution at a dose of 65 mg/kg. After the injection, the rats were fed in single cages, and urine sugar and blood sugar were detected at the 48th hour. When urine sugar was +++ or above, and blood glucose was higher than 16.7 mmol/L, the model establishment requirement is reached. The diabetic retinopathy model was successfully established by detecting blood glucose, urine glucose, and urine volume and retinal VEGF immunohistochemistry.

15 rats were randomly divided into three groups, which were labeled as a control group, and fusion protein I, protein II, protein III, protein IV and protein V treatment groups. The administration was performed via intravitreal injection once every 5 days for 2 weeks, in which the control group was injected with physiological saline (0.1 mL), and the fusion protein I, protein II, protein III, protein IV, and protein V were all administered with 100 µg (0.1 mL). Observation was performed on week 4, week 8, and week 12. The experimental results are shown in Table 23.

TABLE 23

Effect of fusion protein I, protein II, protein III, protein IV, protein V on neovascularization in diabetic retinopathy rat model

| Group (n = 5) | Week 4 | Week 8 | Week 12 |
|---|---|---|---|
| Protein I | 181.15 ± 3.16 | 219.96 ± 3.59 | 262.49 ± 1.21 |
| Protein II | 190.94 ± 2.53 | 217.42 ± 4.48 | 255.17 ± 3.54 |
| Protein III | 179.33 ± 2.54 | 220.03 ± 3.61 | 257.38 ± 1.19 |
| Protein IV | 189.35 ± 2.48 | 225.43 ± 4.32 | 261.22 ± 2.91 |
| Protein V | 187.33 ± 2.39 | 221.49 ± 3.82 | 256.30 ± 3.24 |
| control | 201.69 ± 4.17 | 206.93 ± 1.04 | 196.25 ± 3.56 |

The results showed that under an optical microscope, the number of ganglion cells in 10 retina of posterior pole in each eyeball was counted, and the thickness of 10 retina of posterior pole in each eyeball was measured. Compared with the control group, the thickness of each layer of the retinal tissue of the experimental group was increased. Compared with the control group, the number of ganglion cells in the retinal of rats in the experimental group was increased. Compared with the control group, the number of visual cells in the treatment group was increased. It was indicated that fusion protein I, protein II, protein III, protein IV and protein V could produce a certain therapeutic effect on diabetic retinopathy at 100 µg dose.

What is claimed is:

1. A fusion protein comprising an antiangiogenesis polypeptide sequence and an Fc sequence of an antibody IgG1, wherein the amino acid sequence of the fusion protein comprises SEQ ID NO: 15.

2. A gene encoding the fusion protein according to claim 1, wherein the nucleic acid sequences encoding SEQ ID NO: 15 comprises SEQ ID NO: 16.

3. A method of preparation of a medicament for treating tumors, autoimmune diseases, inflammations and ophthalmic diseases using the composition of claim 1.

4. The method according to claim 3, wherein the tumors include gastric cancer, lung cancer, liver cancer, breast cancer, colon cancer, glioma, melanoma, and cervical cancer, as well as primary or secondary cancer, melanoma and sarcoma originating from the head and neck, brain, thyroid, esophagus, pancreas, lung, liver, stomach, breast, kidney, gallbladder, colon or rectum, ovary, cervix, uterus, prostate, bladder and testicle in human.

5. The method according to claim 3, wherein the inflammations include rheumatoid arthritis, osteoarthritis, gouty arthritis, ankylosing spondylitis, psoriatic arthritis, reactive arthritis, infectious arthritis and traumatic arthritis; and the autoimmune diseases include lupus erythematosus and psoriasis.

6. The method use according to claim 3, wherein the ophthalmic diseases include iris neovascular eye disease, choroidal neovascular eye disease, retinal neovascular eye disease, or corneal neovascular eye disease.

7. The method according to claim 6, wherein the iris neovascular eye disease includes iris neovascular eye diseases caused by neovascular glaucoma, diabetic retinopathy or central retinal vein occlusion; the choroidal neovascular eye disease includes age-related macular degeneration, central exudative chorioretinopathy, ocular histoplasmosis syndrome or serpiginous choroidopathy; the retinal neovascular eye disease includes the retinal neovascular eye diseases associated with diabetes, tumors, retinal detachment, central retinal vein occlusion, retinal periphlebitis, systemic lupus erythematosus, Eales diseases or Coat diseases; the corneal neovascular eye disease includes the corneal neovascular eye diseases caused by cornea contacting an lens, as well as the corneal neovascular eye diseases caused by alkali and other chemical burns, corneal surgery, bacterial infection, chlamydial infection, viral infection or protozoal infection.

8. The method according to claim 3, wherein a dosage form of the medicament is a capsule, a tablet, a pill, an injection, a nasal spray or an aerosol.

* * * * *

SEQUENCE LISTING

<160> NUMBER OF SEQ ID NOS: 25

<210> SEQ ID NO 1
<211> LENGTH: 3
<212> TYPE: PRT

```
<213> ORGANISM: Artificial Sequence
<220> FEATURE:
<223> OTHER INFORMATION: synthesized

<400> SEQUENCE: 1

Arg Gly Asp
1

<210> SEQ ID NO 2
<211> LENGTH: 9
<212> TYPE: DNA
<213> ORGANISM: Artificial Sequence
<220> FEATURE:
<223> OTHER INFORMATION: synthesized

<400> SEQUENCE: 2 cgtggtgac                                                                 9

<210> SEQ ID NO 3
<211> LENGTH: 50
<212> TYPE: PRT
<213> ORGANISM: Artificial Sequence
<220> FEATURE:
<223> OTHER INFORMATION: synthesized

<400> SEQUENCE: 3

Phe Gln Pro Val Leu His Leu Val Ala Leu Asn Ser Pro Leu Ser Gly
1               5                   10                  15

Gly Met Arg Gly Ile Arg Gly Ala Asp Phe Gln Cys Phe Gln Gln Ala
            20                  25                  30

Arg Ala Val Gly Leu Ala Gly Thr Phe Arg Ala Gly Gly Gly Arg
        35                  40                  45

Gly Asp
    50

<210> SEQ ID NO 4
<211> LENGTH: 150
<212> TYPE: DNA
<213> ORGANISM: Artificial Sequence
<220> FEATURE:
<223> OTHER INFORMATION: synthesized

<400> SEQUENCE: 4
ttccaacctg ttcttcacct tgttgctctt aactctcctc tttctggtgg tatgcgtggt        60
atccgtggtg ctgacttcca atgcttccaa caagctcgtg ctgttggtct tgctggtact       120
ttccgtgctg gtggtggtgg tcgtggtgac                                         150

<210> SEQ ID NO 5
<211> LENGTH: 50
<212> TYPE: PRT
<213> ORGANISM: Artificial Sequence
<220> FEATURE:
<223> OTHER INFORMATION: synthesized

<400> SEQUENCE: 5

Arg Gly Asp Gly Gly Gly Gly Phe Gln Pro Val Leu His Leu Val Ala
1               5                   10                  15

Leu Asn Ser Pro Leu Ser Gly Gly Met Arg Gly Ile Arg Gly Ala Asp
            20                  25                  30

Phe Gln Cys Phe Gln Gln Ala Arg Ala Val Gly Leu Ala Gly Thr Phe
        35                  40                  45

Arg Ala
```

<210> SEQ ID NO 6
<211> LENGTH: 150
<212> TYPE: DNA
<213> ORGANISM: Artificial Sequence
<220> FEATURE:
<223> OTHER INFORMATION: synthesized

<400> SEQUENCE: 6

```
cgtggtgacg gtggtggtgg tttccaacct gttcttcacc ttgttgctct taactctcct      60
ctttctggtg gtatgcgtgg tatccgtggt gctgacttcc aatgcttcca acaagctcgt     120
gctgttggtc ttgctggtac tttccgtgct                                      150
```

<210> SEQ ID NO 7
<211> LENGTH: 232
<212> TYPE: PRT
<213> ORGANISM: Artificial Sequence
<220> FEATURE:
<223> OTHER INFORMATION: synthesized

<400> SEQUENCE: 7

```
Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

Lys Asp Thr Leu Met Ile Ser Arg Thr Pro Glu Val Thr Cys Val Val
        35                  40                  45

Val Asp Val Ser His Glu Asp Pro Glu Val Lys Phe Asn Trp Tyr Val
    50                  55                  60

Asp Gly Val Glu Val His Asn Ala Lys Thr Lys Pro Arg Glu Glu Gln
65                  70                  75                  80

Tyr Asn Ser Thr Tyr Arg Val Val Ser Val Leu Thr Val Leu His Gln
                85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys
225                 230
```

<210> SEQ ID NO 8
<211> LENGTH: 696
<212> TYPE: DNA
<213> ORGANISM: Artificial Sequence
<220> FEATURE:

<223> OTHER INFORMATION: synthesized

<400> SEQUENCE: 8

```
gagcccaaat cttgtgacaa aactcacaca tgcccaccgt gcccagcacc tgaactcctg      60
gggggaccgt cagtcttcct cttcccccca aaacccaagg acaccctcat gatctcccgg     120
acccctgagg tcacatgcgt ggtggtggac gtgagccacg aagaccctga ggtcaagttc     180
aactggtacg tggacggcgt ggaggtgcat aatgccaaga caaagccgcg ggaggagcag     240
tacaacagca cgtaccgtgt ggtcagcgtc ctcaccgtcc tgcaccagga ctggctgaat     300
ggcaaggagt acaagtgcaa ggtctccaac aaagccctcc cagcccccat cgagaaaacc     360
atctccaaag ccaaagggca gccccgagaa ccacaggtgt acaccctgcc cccatcccgg     420
gatgagctga ccaagaacca ggtcagcctg acctgcctgg tcaaaggctt ctatcccagc     480
gacatcgccg tggagtggga gagcaatggg cagccggaga caactacaa gaccacgcct      540
cccgtgctgg actccgacgg ctccttcttc ctctacagca agctcaccgt ggacaagagc     600
aggtggcagc aggggaacgt cttctcatgc tccgtgatgc atgaggctct gcacaaccac     660
tacacgcaga agagcctctc cctgtctccg ggtaaa                              696
```

<210> SEQ ID NO 9
<211> LENGTH: 228
<212> TYPE: PRT
<213> ORGANISM: Artificial Sequence
<220> FEATURE:
<223> OTHER INFORMATION: synthesized

<400> SEQUENCE: 9

```
Glu Arg Lys Cys Cys Val Glu Cys Pro Pro Cys Pro Ala Pro Pro Val
  1               5                  10                  15

Ala Gly Pro Ser Val Phe Leu Phe Pro Pro Lys Pro Lys Asp Thr Leu
             20                  25                  30

Met Ile Ser Arg Thr Pro Glu Val Thr Cys Val Val Val Asp Val Ser
         35                  40                  45

His Glu Asp Pro Glu Val Gln Phe Asn Trp Tyr Val Asp Gly Val Glu
     50                  55                  60

Val His Asn Ala Lys Thr Lys Pro Arg Glu Glu Gln Phe Asn Ser Thr
 65                  70                  75                  80

Phe Arg Val Val Ser Val Leu Thr Val Val His Gln Asp Trp Leu Asn
                 85                  90                  95

Gly Lys Glu Tyr Lys Cys Lys Val Ser Asn Lys Gly Leu Pro Ala Pro
            100                 105                 110

Ile Glu Lys Thr Ile Ser Lys Thr Lys Gly Gln Pro Arg Glu Pro Gln
        115                 120                 125

Val Tyr Thr Leu Pro Pro Ser Arg Glu Glu Met Thr Lys Asn Gln Val
    130                 135                 140

Ser Leu Thr Cys Leu Val Lys Gly Phe Tyr Pro Ser Asp Ile Ser Val
145                 150                 155                 160

Glu Trp Glu Ser Asn Gly Gln Pro Glu Asn Asn Tyr Lys Thr Thr Pro
                165                 170                 175

Pro Met Leu Asp Ser Asp Gly Ser Phe Phe Leu Tyr Ser Lys Leu Thr
            180                 185                 190

Val Asp Lys Ser Arg Trp Gln Gln Gly Asn Val Phe Ser Cys Ser Val
        195                 200                 205

Met His Glu Ala Leu His Asn His Tyr Thr Gln Lys Ser Leu Ser Leu
    210                 215                 220
```

Ser Pro Gly Lys
225

<210> SEQ ID NO 10
<211> LENGTH: 684
<212> TYPE: DNA
<213> ORGANISM: Artificial Sequence
<220> FEATURE:
<223> OTHER INFORMATION: synthesized

<400> SEQUENCE: 10

```
gagcgcaaat gttgtgtcga gtgcccaccg tgcccagcac cacctgtggc aggaccgtca    60
gtcttcctct tccccccaaa acccaaggac accctcatga tctcccggac ccctgaggtc   120
acgtgcgtgg tggtggacgt gagccacgaa gaccccgagg tccagttcaa ctggtacgtg   180
gacggcgtgg aggtgcataa tgccaagaca aagccacggg aggagcagtt caacagcacg   240
ttccgtgtgg tcagcgtcct caccgtcgtg caccaggact ggctgaacgg caaggagtac   300
aagtgcaagg tctccaacaa aggcctccca gcccccatcg agaaaaccat ctccaaaacc   360
aaagggcagc cccgagaacc acaggtgtac accctgcccc catcccggga ggagatgacc   420
aagaaccagg tcagcctgac ctgcctggtc aaaggcttct accccagcga catctccgtg   480
gagtgggaga gcaatgggca gccggagaac aactacaaga ccacgcctcc catgctggac   540
tccgacggct ccttcttcct ctacagcaag ctcaccgtgg acaagagcag gtggcagcag   600
gggaacgtct tctcatgctc cgtgatgcat gaggctctgc acaaccacta cacgcagaag   660
agcctctccc tgtctccggg taaa                                          684
```

<210> SEQ ID NO 11
<211> LENGTH: 229
<212> TYPE: PRT
<213> ORGANISM: Artificial Sequence
<220> FEATURE:
<223> OTHER INFORMATION: synthesized

<400> SEQUENCE: 11

Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160

Ala Val Glu Trp Glu Ser Asn Gly Gln Pro Glu Asn Asn Tyr Lys Thr

```
                165                 170                 175
Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly
225

<210> SEQ ID NO 12
<211> LENGTH: 684
<212> TYPE: DNA
<213> ORGANISM: Artificial Sequence
<220> FEATURE:
<223> OTHER INFORMATION: synthesized

<400> SEQUENCE: 12
gccgagtcta agtacggccc tccttgccca ccttgccctg ctccagaagc tgctggcggc      60
ccttccgtgt tcctgttccc cccaaagccc aaggacaccc tgatgatctc ccggaccccc     120
gaagtgacct gcgtggtggt ggatgtgtcc caggaagatc ccgaggtgca gttcaattgg     180
tacgtggacg gcgtggaagt gcacaacgcc aagaccaagc cagagagga acagttcaac      240 tccacctacc gggtggtgtc cgtgctgacc gtgctgcacc aggattggct gaacggcaaa     300
gagtacaagt gcaaggtgtc caacaagggc ctgccctcca gcatcgaaaa gaccatctcc     360
aaggccaagg gccagccccg ggaacccag gtgtacacac tgcctccaag ccaggaagag      420
atgaccaaga accaggtgtc cctgacctgt ctcgtgaagg gcttctaccc ctccgatatc     480
gccgtggaat gggagtccaa cggccagcct gagaacaact acaagaccac ccccctgtg     540 ctggactccg acggctcctt cttcctgtac tcccgcctga ccgtggacaa gtccagatgg     600
caggaaggca acgtgttctc ctgctccgtg atgcacgagg ccctgcacaa ccactacacc     660
cagaagtccc tgtccctgtc tctg                                             684

<210> SEQ ID NO 13
<211> LENGTH: 245
<212> TYPE: PRT
<213> ORGANISM: Artificial Sequence
<220> FEATURE:
<223> OTHER INFORMATION: synthesized

<400> SEQUENCE: 13

Arg Asn Thr Gly Arg Gly Gly Glu Glu Lys Lys Lys Glu Lys Glu Lys
1               5                   10                  15

Glu Glu Gln Glu Glu Arg Glu Thr Lys Thr Pro Glu Cys Pro Ser His
            20                  25                  30

Thr Gln Pro Leu Gly Val Phe Leu Phe Pro Pro Lys Pro Lys Asp Thr
        35                  40                  45

Leu Met Ile Ser Arg Thr Pro Glu Val Thr Cys Val Val Val Asp Val
    50                  55                  60

Ser Gln Glu Asp Pro Glu Val Gln Phe Asn Trp Tyr Val Asp Gly Val
65                  70                  75                  80

Glu Val His Asn Ala Lys Thr Lys Pro Arg Glu Glu Gln Phe Asn Ser
                85                  90                  95

Thr Tyr Arg Val Val Ser Val Leu Thr Val Leu His Gln Asp Trp Leu
            100                 105                 110
```

Asn Gly Lys Glu Tyr Lys Cys Lys Val Ser Asn Lys Gly Leu Pro Ser
            115                 120                 125

Ser Ile Glu Lys Thr Ile Ser Lys Ala Lys Gly Gln Pro Arg Glu Pro
    130                 135                 140

Gln Val Tyr Thr Leu Pro Pro Ser Gln Glu Glu Met Thr Lys Asn Gln
145                 150                 155                 160

Val Ser Leu Thr Cys Leu Val Lys Gly Phe Tyr Pro Ser Asp Ile Ala
                165                 170                 175

Val Glu Trp Glu Ser Asn Gly Gln Pro Glu Asn Asn Tyr Lys Thr Thr
            180                 185                 190

Pro Pro Val Leu Asp Ser Asp Gly Ser Phe Phe Leu Tyr Ser Arg Leu
        195                 200                 205

Thr Val Asp Lys Ser Arg Trp Gln Glu Gly Asn Val Phe Ser Cys Ser
    210                 215                 220

Val Met His Glu Ala Leu His Asn His Tyr Thr Gln Lys Ser Leu Ser
225                 230                 235                 240

Leu Ser Leu Gly Lys
            245

<210> SEQ ID NO 14
<211> LENGTH: 735
<212> TYPE: DNA
<213> ORGANISM: Artificial Sequence
<220> FEATURE:
<223> OTHER INFORMATION: synthesized

<400> SEQUENCE: 14
agaaatactg gcagaggcgg cgaggaaaag aagaaagaga agaaaaaga ggaacaggaa      60 gagagagaga ctaagacccc cgagtgcccc tcccacacac agcctctggg cgtgttcctg    120
tttcccccaa agcccaagga caccctgatg atctcccgga cccccgaagt gacctgcgtg    180
gtggtggatg tgtcccagga agatcccgag gtgcagttca attggtacgt ggacggcgtg    240
gaagtgcaca acgccaagac caagccccgc gaggaacagt tcaactccac ctaccgggtg    300
gtgtccgtgc tgaccgtgct gcaccaggat tggctgaacg gcaaagagta caagtgcaag    360
gtgtccaaca agggcctgcc ctccagcatc gaaaagacca tctccaaggc caagggccag    420
ccccgggaac cccaggtgta cactgcct ccaagccagg aagaaatgac caagaaccag    480
gtgtccctga cctgtctcgt gaagggcttc taccctccg atatcgccgt ggaatgggag    540
tccaacggcc agcctgagaa caactacaag accacccccc ctgtgctgga ctccgacggc    600
tccttcttcc tgtactcccg cctgaccgtg gacaagtcca gatggcagga aggcaacgtg    660
ttctcctgct ccgtgatgca cgaggccctg cacaaccact acacccagaa gtccctgtcc    720
ctgtctctgg gcaag                                                    735

<210> SEQ ID NO 15
<211> LENGTH: 297
<212> TYPE: PRT
<213> ORGANISM: Artificial Sequence
<220> FEATURE:
<223> OTHER INFORMATION: synthesized

<400> SEQUENCE: 15

Glu Pro Lys Ser Cys Asp Lys Thr His Thr Cys Pro Pro Cys Pro Ala
1               5                   10                  15

Pro Glu Leu Leu Gly Gly Pro Ser Val Phe Leu Phe Pro Pro Lys Pro
            20                  25                  30

```
Lys Asp Thr Leu Met Ile Ser Arg Thr Pro Glu Val Thr Cys Val Val
             35                  40                  45

Val Asp Val Ser His Glu Asp Pro Glu Val Lys Phe Asn Trp Tyr Val
 50                  55                  60

Asp Gly Val Glu Val His Asn Ala Lys Thr Lys Pro Arg Glu Glu Gln
65                   70                  75                  80

Tyr Asn Ser Thr Tyr Arg Val Val Ser Val Leu Thr Val Leu His Gln
                 85                  90                  95

Asp Trp Leu Asn Gly Lys Glu Tyr Lys Cys Lys Val Ser Asn Lys Ala
            100                 105                 110

Leu Pro Ala Pro Ile Glu Lys Thr Ile Ser Lys Ala Lys Gly Gln Pro
        115                 120                 125

Arg Glu Pro Gln Val Tyr Thr Leu Pro Pro Ser Arg Asp Glu Leu Thr
    130                 135                 140

Lys Asn Gln Val Ser Leu Thr Cys Leu Val Lys Gly Phe Tyr Pro Ser
145                 150                 155                 160

Asp Ile Ala Val Glu Trp Glu Ser Asn Gly Gln Pro Glu Asn Asn Tyr
                165                 170                 175

Lys Thr Thr Pro Pro Val Leu Asp Ser Asp Gly Ser Phe Phe Leu Tyr
            180                 185                 190

Ser Lys Leu Thr Val Asp Lys Ser Arg Trp Gln Gln Gly Asn Val Phe
        195                 200                 205

Ser Cys Ser Val Met His Glu Ala Leu His Asn His Tyr Thr Gln Lys
    210                 215                 220

Ser Leu Ser Leu Ser Pro Gly Lys Gly Gly Gly Ser Gly Gly Gly
225                 230                 235                 240

Gly Ser Gly Gly Gly Gly Ser Phe Gln Pro Val Leu His Leu Val Ala
                245                 250                 255

Leu Asn Ser Pro Leu Ser Gly Gly Met Arg Gly Ile Arg Gly Ala Asp
            260                 265                 270

Phe Gln Cys Phe Gln Gln Ala Arg Ala Val Gly Leu Ala Gly Thr Phe
        275                 280                 285

Arg Ala Gly Gly Gly Gly Arg Gly Asp
    290                 295
```

<210> SEQ ID NO 16
<211> LENGTH: 891
<212> TYPE: DNA
<213> ORGANISM: Artificial Sequence
<220> FEATURE:
<223> OTHER INFORMATION: synthesized

<400> SEQUENCE: 16

```
gagcccaaat cttgtgacaa aactcacaca tgcccaccgt gcccagcacc tgaactcctg      60
gggggaccgt cagtcttcct cttccccccca aaacccaagg acaccctcat gatctcccgg    120 accccctgagg tcacatgcgt ggtggtggac gtgagccacg aagaccctga ggtcaagttc    180
aactggtacg tggacggcgt ggaggtgcat aatgccaaga caaagccgcg ggaggagcag    240
tacaacagca cgtaccgtgt ggtcagcgtc ctcaccgtcc tgcaccagga ctggctgaat    300
ggcaaggagt acaagtgcaa ggtctccaac aaagccctcc cagcccccat cgagaaaacc    360
atctccaaag ccaaagggca gccccgagaa ccacaggtgt acaccctgcc cccatcccgg    420
gatgagctga ccaagaacca ggtcagcctg acctgcctgg tcaaaggctt ctatcccagc    480
gacatcgccg tggagtggga gagcaatggg cagccggaga acaactacaa gaccacgcct    540
```

```
cccgtgctgg actccgacgg ctccttcttc ctctacagca agctcaccgt ggacaagagc    600
aggtggcagc aggggaacgt cttctcatgc tccgtgatgc atgaggctct gcacaaccac    660
tacacgcaga agagcctctc cctgtctccg ggtaaaggcg gcggaggatc tggcggaggc    720
ggttctggtg gtggtggctc tttccaacct gttcttcacc ttgttgctct taactctcct    780
ctttctggtg gtatgcgtgg tatccgtggt gctgacttcc aatgcttcca acaagctcgt    840
gctgttggtc ttgctggtac tttccgtgct ggtggtggtg gtcgtggtga c             891
```

```
<210> SEQ ID NO 17
<211> LENGTH: 293
<212> TYPE: PRT
<213> ORGANISM: Artificial Sequence
<220> FEATURE:
<223> OTHER INFORMATION: synthesized

<400> SEQUENCE: 17
```

| | | | | | | | | | | | | | | |
|---|---|---|---|---|---|---|---|---|---|---|---|---|---|---|
| Glu | Arg | Lys | Cys | Cys | Val | Glu | Cys | Pro | Pro | Cys | Pro | Ala | Pro | Val |
| 1 | | | | 5 | | | | | 10 | | | | | 15 |
| Ala | Gly | Pro | Ser | Val | Phe | Leu | Phe | Pro | Pro | Lys | Pro | Lys | Asp | Thr | Leu |
| | | | 20 | | | | | 25 | | | | | 30 | | |
| Met | Ile | Ser | Arg | Thr | Pro | Glu | Val | Thr | Cys | Val | Val | Asp | Val | Ser |
| | | | 35 | | | | | 40 | | | | | 45 | | |
| His | Glu | Asp | Pro | Glu | Val | Gln | Phe | Asn | Trp | Tyr | Val | Asp | Gly | Val | Glu |
| 50 | | | | | 55 | | | | | 60 | | | | | |
| Val | His | Asn | Ala | Lys | Thr | Lys | Pro | Arg | Glu | Glu | Gln | Phe | Asn | Ser | Thr |
| 65 | | | | | 70 | | | | | 75 | | | | | 80 |
| Phe | Arg | Val | Val | Ser | Val | Leu | Thr | Val | Val | His | Gln | Asp | Trp | Leu | Asn |
| | | | | 85 | | | | | 90 | | | | | 95 | |
| Gly | Lys | Glu | Tyr | Lys | Cys | Lys | Val | Ser | Asn | Lys | Gly | Leu | Pro | Ala | Pro |
| | | | | 100 | | | | | 105 | | | | | 110 | |
| Ile | Glu | Lys | Thr | Ile | Ser | Lys | Thr | Lys | Gly | Gln | Pro | Arg | Glu | Pro | Gln |
| | | | | 115 | | | | | 120 | | | | | 125 | |
| Val | Tyr | Thr | Leu | Pro | Pro | Ser | Arg | Glu | Glu | Met | Thr | Lys | Asn | Gln | Val |
| 130 | | | | | 135 | | | | | 140 | | | | | |
| Ser | Leu | Thr | Cys | Leu | Val | Lys | Gly | Phe | Tyr | Pro | Ser | Asp | Ile | Ser | Val |
| 145 | | | | | 150 | | | | | 155 | | | | | 160 |
| Glu | Trp | Glu | Ser | Asn | Gly | Gln | Pro | Glu | Asn | Asn | Tyr | Lys | Thr | Thr | Pro |
| | | | | 165 | | | | | 170 | | | | | 175 | |
| Pro | Met | Leu | Asp | Ser | Asp | Gly | Ser | Phe | Phe | Leu | Tyr | Ser | Lys | Leu | Thr |
| | | | 180 | | | | | 185 | | | | | 190 | | |
| Val | Asp | Lys | Ser | Arg | Trp | Gln | Gln | Gly | Asn | Val | Phe | Ser | Cys | Ser | Val |
| | | | 195 | | | | | 200 | | | | | 205 | | |
| Met | His | Glu | Ala | Leu | His | Asn | His | Tyr | Thr | Gln | Lys | Ser | Leu | Ser | Leu |
| | | | 210 | | | | | 215 | | | | | 220 | | |
| Ser | Pro | Gly | Lys | Gly | Gly | Gly | Ser | Gly | Gly | Gly | Gly | Ser | Gly | Gly |
| 225 | | | | | 230 | | | | | 235 | | | | | 240 |
| Gly | Gly | Ser | Phe | Gln | Pro | Val | Leu | His | Leu | Val | Ala | Leu | Asn | Ser | Pro |
| | | | | 245 | | | | | 250 | | | | | 255 | |
| Leu | Ser | Gly | Gly | Met | Arg | Gly | Ile | Arg | Gly | Ala | Asp | Phe | Gln | Cys | Phe |
| | | | | 260 | | | | | 265 | | | | | 270 | |
| Gln | Gln | Ala | Arg | Ala | Val | Gly | Leu | Ala | Gly | Thr | Phe | Arg | Ala | Gly | Gly |
| | | | 275 | | | | | 280 | | | | | 285 | | |
| Gly | Gly | Arg | Gly | Asp |
| | | 290 | | |

<210> SEQ ID NO 18
<211> LENGTH: 879
<212> TYPE: DNA
<213> ORGANISM: Artificial Sequence
<220> FEATURE:
<223> OTHER INFORMATION: synthesized

<400> SEQUENCE: 18

```
gagcgcaaat gttgtgtcga gtgcccaccg tgcccagcac cacctgtggc aggaccgtca    60
gtcttcctct tccccccaaa acccaaggac accctcatga tctcccggac ccctgaggtc   120
acgtgcgtgg tggtggacgt gagccacgaa gaccccgagg tccagttcaa ctggtacgtg   180
gacggcgtgg aggtgcataa tgccaagaca aagccacggg aggagcagtt caacagcacg   240
ttccgtgtgg tcagcgtcct caccgtcgtg caccaggact ggctgaacgg caaggagtac   300
aagtgcaagg tctccaacaa aggcctccca gcccccatcg agaaaaccat ctccaaaacc   360
aaagggcagc cccgagaacc acaggtgtac accctgcccc catcccggga ggagatgacc   420
aagaaccagg tcagcctgac ctgcctggtc aaaggcttct accccagcga catctccgtg   480
gagtgggaga gcaatgggca gccggagaac aactacaaga ccacgcctcc catgctggac   540
tccgacggct ccttcttcct ctacagcaag ctcaccgtgg acaagagcag gtggcagcag   600
gggaacgtct tctcatgctc cgtgatgcat gaggctctgc acaaccacta cacgcagaag   660
agcctctccc tgtctccggg taaaggcggc ggaggatctg gcggaggcgg ttctggtggt   720
ggtggctctt ccaacctgt tcttcacctt gttgctctta actctcctct ttctggtggt   780
atgcgtggta tccgtggtgc tgacttccaa tgcttccaac aagctcgtgc tgttggtctt   840
gctggtactt tccgtgctgg tggtggtggt cgtggtgac                          879
```

<210> SEQ ID NO 19
<211> LENGTH: 294
<212> TYPE: PRT
<213> ORGANISM: Artificial Sequence
<220> FEATURE:
<223> OTHER INFORMATION: synthesized

<400> SEQUENCE: 19

```
Ala Glu Ser Lys Tyr Gly Pro Pro Cys Pro Pro Cys Pro Ala Pro Glu
1               5                   10                  15

Ala Ala Gly Gly Pro Ser Val Phe Leu Phe Pro Pro Lys Pro Lys Asp
            20                  25                  30

Thr Leu Met Ile Ser Arg Thr Pro Glu Val Thr Cys Val Val Val Asp
        35                  40                  45

Val Ser Gln Glu Asp Pro Glu Val Gln Phe Asn Trp Tyr Val Asp Gly
    50                  55                  60

Val Glu Val His Asn Ala Lys Thr Lys Pro Arg Glu Glu Gln Phe Asn
65                  70                  75                  80

Ser Thr Tyr Arg Val Val Ser Val Leu Thr Val Leu His Gln Asp Trp
                85                  90                  95

Leu Asn Gly Lys Glu Tyr Lys Cys Lys Val Ser Asn Lys Gly Leu Pro
            100                 105                 110

Ser Ser Ile Glu Lys Thr Ile Ser Lys Ala Lys Gly Gln Pro Arg Glu
        115                 120                 125

Pro Gln Val Tyr Thr Leu Pro Pro Ser Gln Glu Glu Met Thr Lys Asn
    130                 135                 140

Gln Val Ser Leu Thr Cys Leu Val Lys Gly Phe Tyr Pro Ser Asp Ile
145                 150                 155                 160
```

```
Ala Val Glu Trp Glu Ser Asn Gly Gln Pro Glu Asn Asn Tyr Lys Thr
                165                 170                 175

Thr Pro Pro Val Leu Asp Ser Asp Gly Ser Phe Phe Leu Tyr Ser Arg
            180                 185                 190

Leu Thr Val Asp Lys Ser Arg Trp Gln Glu Gly Asn Val Phe Ser Cys
        195                 200                 205

Ser Val Met His Glu Ala Leu His Asn His Tyr Thr Gln Lys Ser Leu
    210                 215                 220

Ser Leu Ser Leu Gly Gly Gly Gly Ser Gly Gly Gly Ser Gly
225                 230                 235                 240

Gly Gly Gly Ser Phe Gln Pro Val Leu His Leu Val Ala Leu Asn Ser
                245                 250                 255

Pro Leu Ser Gly Gly Met Arg Gly Ile Arg Gly Ala Asp Phe Gln Cys
            260                 265                 270

Phe Gln Gln Ala Arg Ala Val Gly Leu Ala Gly Thr Phe Arg Ala Gly
        275                 280                 285

Gly Gly Gly Arg Gly Asp
    290

<210> SEQ ID NO 20
<211> LENGTH: 882
<212> TYPE: DNA
<213> ORGANISM: Artificial Sequence
<220> FEATURE:
<223> OTHER INFORMATION: synthesized

<400> SEQUENCE: 20
gccgagtcta agtacggccc tccttgccca ccttgccctg ctccagaagc tgctggcggc     60
ccttccgtgt tcctgttccc cccaaagccc aaggacaccc tgatgatctc ccggaccccc    120
gaagtgacct gcgtggtggt ggatgtgtcc caggaagatc ccgaggtgca gttcaattgg    180
tacgtggacg gcgtggaagt gcacaacgcc aagaccaagc ccagagagga acagttcaac    240
tccacctacc gggtggtgtc cgtgctgacc gtgctgcacc aggattggct gaacggcaaa    300
gagtacaagt gcaaggtgtc caacaagggc ctgcccctcca gcatcgaaaa gaccatctcc    360
aaggccaagg gccagccccg ggaaccccag gtgtacacac tgcctccaag ccaggaagag    420
atgaccaaga accaggtgtc cctgacctgt ctcgtgaagg gcttctaccc ctccgatatc    480
gccgtggaat gggagtccaa cggccagcct gagaacaact acaagaccac ccccctgtg     540 ctggactccg acggctcctt cttcctgtac tcccgcctga ccgtggacaa gtccagatgg    600
caggaaggca acgtgttctc ctgctccgtg atgcacgagg ccctgcacaa ccactacacc    660
cagaagtccc tgtccctgtc tctgggcggc ggcggaggat ctggcggagg cggttctggt    720
ggtggtggct ctttccaacc tgttcttcac cttgttgctc ttaactctcc tctttctggt    780
ggtatgcgtg gtatccgtgg tgctgacttc caatgcttcc aacaagctcg tgctgttggt    840
cttgctggta ctttccgtgc tggtggtggt ggtcgtggtg ac                       882

<210> SEQ ID NO 21
<211> LENGTH: 295
<212> TYPE: PRT
<213> ORGANISM: Artificial Sequence
<220> FEATURE:
<223> OTHER INFORMATION: synthesized

<400> SEQUENCE: 21

Arg Asn Thr Gly Arg Gly Gly Glu Glu Lys Lys Lys Glu Lys Glu Lys
```

```
  1               5                  10                 15
Glu Glu Gln Glu Glu Arg Glu Thr Lys Thr Pro Glu Cys Pro Ser His
                20                 25                 30

Thr Gln Pro Leu Gly Val Phe Leu Phe Pro Pro Lys Pro Lys Asp Thr
                35                 40                 45

Leu Met Ile Ser Arg Thr Pro Glu Val Thr Cys Val Val Val Asp Val
 50                 55                 60

Ser Gln Glu Asp Pro Glu Val Gln Phe Asn Trp Tyr Val Asp Gly Val
 65                 70                 75                 80

Glu Val His Asn Ala Lys Thr Lys Pro Arg Glu Glu Gln Phe Asn Ser
                85                 90                 95

Thr Tyr Arg Val Val Ser Val Leu Thr Val Leu His Gln Asp Trp Leu
                100                105                110

Asn Gly Lys Glu Tyr Lys Cys Lys Val Ser Asn Lys Gly Leu Pro Ser
                115                120                125

Ser Ile Glu Lys Thr Ile Ser Lys Ala Lys Gly Gln Pro Arg Glu Pro
130                135                140

Gln Val Tyr Thr Leu Pro Pro Ser Gln Glu Glu Met Thr Lys Asn Gln
145                150                155                160

Val Ser Leu Thr Cys Leu Val Lys Gly Phe Tyr Pro Ser Asp Ile Ala
                165                170                175

Val Glu Trp Glu Ser Asn Gly Gln Pro Glu Asn Asn Tyr Lys Thr Thr
                180                185                190

Pro Pro Val Leu Asp Ser Asp Gly Ser Phe Phe Leu Tyr Ser Arg Leu
                195                200                205

Thr Val Asp Lys Ser Arg Trp Gln Glu Gly Asn Val Phe Ser Cys Ser
210                215                220

Val Met His Glu Ala Leu His Asn His Tyr Thr Gln Lys Ser Leu Ser
225                230                235                240

Leu Ser Leu Gly Lys Phe Gln Pro Val Leu His Leu Val Ala Leu Asn
                245                250                255

Ser Pro Leu Ser Gly Gly Met Arg Gly Ile Arg Gly Ala Asp Phe Gln
                260                265                270

Cys Phe Gln Gln Ala Arg Ala Val Gly Leu Ala Gly Thr Phe Arg Ala
                275                280                285

Gly Gly Gly Gly Arg Gly Asp
                290                295

<210> SEQ ID NO 22
<211> LENGTH: 885
<212> TYPE: DNA
<213> ORGANISM: Artificial Sequence
<220> FEATURE:
<223> OTHER INFORMATION: synthesized

<400> SEQUENCE: 22
agaaatactg gcagaggcgg cgaggaaaag aagaaagaga agaaaaaga ggaacaggaa        60 gagagagaga ctaagacccc cgagtgcccc tcccacacac agcctctggg cgtgttcctg      120
tttcccccaa agcccaagga caccctgatg atctcccgga cccccgaagt gacctgcgtg      180
gtggtggatg tgtcccagga agatcccgag gtgcagttca attggtacgt ggacggcgtg      240
gaagtgcaca acgccaagac caagccccgc gaggaacagt tcaactccac ctaccgggtg      300
gtgtccgtgc tgaccgtgct gcaccaggat tggctgaacg gcaaagagta caagtgcaag      360
gtgtccaaca agggcctgcc ctccagcatc gaaaagacca tctccaaggc caagggccag      420
```

```
cccgggaac ccaggtgta cacactgcct ccaagccagg aagaaatgac caagaaccag    480
gtgtccctga cctgtctcgt gaagggcttc taccctccg atatcgccgt ggaatgggag    540
tccaacggcc agcctgagaa caactacaag accacccccc ctgtgctgga ctccgacggc    600
tccttcttcc tgtactcccg cctgaccgtg gacaagtcca gatggcagga aggcaacgtg    660
ttctcctgct ccgtgatgca cgaggccctg cacaaccact acacccagaa gtccctgtcc    720
ctgtctctgg gcaagttcca acctgttctt caccttgttg ctcttaactc tcctctttct    780
ggtggtatgc gtggtatccg tggtgctgac ttccaatgct ccaacaagc tcgtgctgtt    840 ggtcttgctg gtactttccg tgctggtggt ggtggtcgtg gtgac    885
```

<210> SEQ ID NO 23
<211> LENGTH: 345
<212> TYPE: PRT
<213> ORGANISM: Artificial Sequence
<220> FEATURE:
<223> OTHER INFORMATION: synthesized

<400> SEQUENCE: 23

```
Arg Gly Asp Gly Gly Gly Gly Phe Gln Pro Val Leu His Leu Val Ala
1               5                   10                  15

Leu Asn Ser Pro Leu Ser Gly Gly Met Arg Gly Ile Arg Gly Ala Asp
            20                  25                  30

Phe Gln Cys Phe Gln Gln Ala Arg Ala Val Gly Leu Ala Gly Thr Phe
        35                  40                  45

Arg Ala Phe Gln Pro Val Leu His Leu Val Ala Leu Asn Ser Pro Leu
    50                  55                  60

Ser Gly Gly Met Arg Gly Ile Arg Gly Ala Asp Phe Gln Cys Phe Gln
65                  70                  75                  80

Gln Ala Arg Ala Val Gly Leu Ala Gly Thr Phe Arg Ala Gly Gly
                85                  90                  95

Gly Arg Gly Asp Arg Asn Thr Gly Arg Gly Gly Glu Glu Lys Lys
            100                 105                 110

Glu Lys Glu Lys Glu Glu Gln Glu Glu Arg Glu Thr Lys Thr Pro Glu
        115                 120                 125

Cys Pro Ser His Thr Gln Pro Leu Gly Val Phe Leu Phe Pro Pro Lys
    130                 135                 140

Pro Lys Asp Thr Leu Met Ile Ser Arg Thr Pro Glu Val Thr Cys Val
145                 150                 155                 160

Val Val Asp Val Ser Gln Glu Asp Pro Glu Val Gln Phe Asn Trp Tyr
                165                 170                 175

Val Asp Gly Val Glu Val His Asn Ala Lys Thr Lys Pro Arg Glu Glu
            180                 185                 190

Gln Phe Asn Ser Thr Tyr Arg Val Val Ser Val Leu Thr Val Leu His
        195                 200                 205

Gln Asp Trp Leu Asn Gly Lys Glu Tyr Lys Cys Lys Val Ser Asn Lys
    210                 215                 220

Gly Leu Pro Ser Ser Ile Glu Lys Thr Ile Ser Lys Ala Lys Gly Gln
225                 230                 235                 240

Pro Arg Glu Pro Gln Val Tyr Thr Leu Pro Pro Ser Gln Glu Glu Met
                245                 250                 255

Thr Lys Asn Gln Val Ser Leu Thr Cys Leu Val Lys Gly Phe Tyr Pro
            260                 265                 270

Ser Asp Ile Ala Val Glu Trp Glu Ser Asn Gly Gln Pro Glu Asn Asn
```

```
                275                 280                 285
Tyr Lys Thr Thr Pro Pro Val Leu Asp Ser Asp Gly Ser Phe Phe Leu
        290                 295                 300

Tyr Ser Arg Leu Thr Val Asp Lys Ser Arg Trp Gln Glu Gly Asn Val
305                 310                 315                 320

Phe Ser Cys Ser Val Met His Glu Ala Leu His Asn His Tyr Thr Gln
                325                 330                 335

Lys Ser Leu Ser Leu Ser Leu Gly Lys
        340                 345
```

```
<210> SEQ ID NO 24
<211> LENGTH: 1035
<212> TYPE: DNA
<213> ORGANISM: Artificial Sequence
<220> FEATURE:
<223> OTHER INFORMATION: synthesized

<400> SEQUENCE: 24
cgtggtgacg gtggtggtgg tttccaacct gttcttcacc tgttgctct  taactctcct       60
ctttctggtg gtatgcgtgg tatccgtggt gctgacttcc aatgcttcca acaagctcgt     120
gctgttggtc ttgctggtac tttccgtgct tccaacctg  ttcttcacct  tgttgctctt     180
aactctcctc tttctggtgg tatgcgtggt atccgtggtg ctgacttcca atgcttccaa     240
caagctcgtg ctgttggtct tgctggtact ttccgtgctg gtggtggtgg tcgtggtgac     300
agaaatactg gcagaggcgg cgaggaaaag aagaaagaga agaaaaaga  ggaacaggaa     360
gagagagaga ctaagacccc cgagtgcccc tcccacacac agcctctggg cgtgttcctg     420
tttcccccaa agcccaagga caccctgatg atctcccgga cccccgaagt gacctgcgtg     480
gtggtggatg tgtcccagga agatcccgag gtgcagttca attggtacgt ggacggcgtg     540
gaagtgcaca acgccaagac caagccccgc gaggaacagt tcaactccac ctaccgggtg     600
gtgtccgtgc tgaccgtgct gcaccaggat tggctgaacg gcaaagagta caagtgcaag     660
gtgtccaaca agggcctgcc ctccagcatc gaaaagacca tctccaaggc caagggccag     720
ccccgggaac cccaggtgta cacactgcct ccaagccagg aagaaatgac caagaaccag     780
gtgtccctga cctgtctcgt gaagggcttc taccccctcc gatatcgccg tggaatggga     840
tccaacggcc agcctgagaa caactacaag accaccccc  ctgtgctgga ctccgacggc     900
tccttcttcc tgtactcccg cctgaccgtg gacaagtcca gatggcagga aggcaacgtg     960
ttctcctgct ccgtgatgca cgaggccctg cacaaccact acacccagaa gtccctgtcc    1020
ctgtctctgg gcaag                                                      1035
```

```
<210> SEQ ID NO 25
<211> LENGTH: 15
<212> TYPE: PRT
<213> ORGANISM: Artificial Sequence
<220> FEATURE:
<223> OTHER INFORMATION: Synthesized

<400> SEQUENCE: 25

Gly Gly Gly Gly Ser Gly Gly Gly Gly Ser Gly Gly Gly Gly Ser
1               5                   10                  15
```